US011684505B2

(12) United States Patent
Rowe

(10) Patent No.: US 11,684,505 B2
(45) Date of Patent: Jun. 27, 2023

(54) TEMPORARY CAST DEVICES COMPRISING ARTIFICIAL MUSCLES

(71) Applicant: Toyota Motor Engineering & Manufacturing North America, Inc., Plano, TX (US)

(72) Inventor: Michael P. Rowe, Pinckney, MI (US)

(73) Assignee: Toyota Motor Engineering & Manufacturing North America, Inc., Plano, TX (US)

( * ) Notice: Subject to any disclaimer, the term of this patent is extended or adjusted under 35 U.S.C. 154(b) by 317 days.

(21) Appl. No.: 16/929,863

(22) Filed: Jul. 15, 2020

(65) Prior Publication Data

US 2022/0015932 A1 Jan. 20, 2022

(51) Int. Cl.
*A61F 5/01* (2006.01)
(52) U.S. Cl.
CPC .... *A61F 5/0102* (2013.01); *A61F 2005/0155* (2013.01); *A61F 2005/0188* (2013.01)
(58) Field of Classification Search
CPC ............ A61F 5/0102; A61F 2005/0155; A61F 2005/0188; A61F 5/05816; A61F 5/32;
(Continued)

(56) References Cited

U.S. PATENT DOCUMENTS

| 6,099,476 A | 8/2000 | Engel |
| 7,056,297 B2 * | 6/2006 | Dohno ................... A63B 24/00 310/317 |

(Continued)

FOREIGN PATENT DOCUMENTS

| CN | 106037870 A | 10/2016 |
| CN | 107981979 A | 5/2018 |

(Continued)

OTHER PUBLICATIONS

Mehmood et al. "A Flexible and Low Power Telemetric Sensing and Monitoring System for Chronic Wound Diagnostics" BioMedical Engineering OnLine. Published: Mar. 1, 2015. (https://biomedical-engineering-online.biomedcentral.com/articles/10.1186/s12938-015-0011-y).

(Continued)

*Primary Examiner* — Rachael E Bredefeld
*Assistant Examiner* — Seth R. Brown
(74) *Attorney, Agent, or Firm* — Dinsmore & Shohl LLP

(57) ABSTRACT

A temporary cast that includes an exterior shell, a lining body including an inner layer, one or more integrated pressure sensors communicatively coupled to a controller, and a plurality of artificial muscles disposed between the inner layer and the exterior shell. Each of the plurality of artificial muscles is communicatively coupled to the controller and includes a housing including an electrode region and an expandable fluid region, a dielectric fluid housed within the housing, and an electrode pair positioned in the electrode region of the housing. The electrode pair includes a first electrode fixed to a first surface of the housing and a second electrode fixed to a second surface of the housing, where the electrode pair is actuatable between a non-actuated and actuated states such that actuation from the non-actuated state to the actuated state directs the dielectric fluid into the expandable fluid region, expanding the expandable fluid region.

18 Claims, 10 Drawing Sheets

(58) Field of Classification Search
CPC ... A61F 5/34; A61H 9/0078; A61H 2011/005; A61H 11/00; A61H 9/00; A61H 2201/5071; A61H 2205/10; A61H 2205/106; A61H 2205/108

See application file for complete search history.

(56) References Cited

U.S. PATENT DOCUMENTS

| | | | |
|---|---|---|---|
| 7,679,261 | B2 | 3/2010 | Chappaz et al. |
| 7,834,527 | B2 | 11/2010 | Alvarez Icaza Rivera et al. |
| 9,615,992 | B2* | 4/2017 | Allen .................. A61H 9/0078 |
| 10,233,910 | B2 | 3/2019 | Mazzeo et al. |
| 2006/0248750 | A1* | 11/2006 | Rosenberg ........... A43B 1/0054 36/29 |
| 2007/0249977 | A1 | 10/2007 | Bonnefin et al. |
| 2008/0033228 | A1* | 2/2008 | Rastegar .............. A61H 9/0092 600/16 |
| 2010/0056966 | A1* | 3/2010 | Toth ....................... A61H 1/008 601/134 |
| 2011/0082401 | A1* | 4/2011 | Iker ...................... A61H 9/0092 601/152 |
| 2013/0085432 | A1* | 4/2013 | Malhi .................. A61H 9/0078 601/151 |
| 2015/0018733 | A1* | 1/2015 | Ben-Meir .......... A41D 13/0512 602/6 |
| 2017/0100300 | A1* | 4/2017 | Rapp .................... A61B 5/6828 |
| 2017/0181882 | A1* | 6/2017 | Chisena .................... A61F 5/30 |
| 2019/0000329 | A1* | 1/2019 | Denson ............. A61B 5/02438 |

FOREIGN PATENT DOCUMENTS

| | | |
|---|---|---|
| CN | 108122232 A | 6/2018 |
| CN | 209812321 U | 12/2019 |
| JP | 2007097292 A | 4/2007 |
| WO | 2019002860 A1 | 1/2019 |
| WO | 2019173227 A1 | 9/2019 |

OTHER PUBLICATIONS

Wulff "Castminder—The Cast and Splint Monitoring System" Published: Oct. 10, 2016. (https://hackaday.io/project/13284-castminder-the-cast-and-splint-monitoring-system).

Shane Mitchell, et al., "An Easy-To-Implement Toolkit To Create Versatile And High-Performance HASEL Actuators For Untethered Soft Robots," Journal Article, Advanced Science 6(14):1900178, Jun. 2019, URL: https://www.researchgate.net/figure/Generalized-principle-of-zipping-mode-actuation-in-HASEL-actuators-As-voltage-is_fig1_333725822, 15 pages.

E. Acome, et al., "Hydraulically Amplified Self-Healing Electrostatic Actuators With Muscle-Like Performance," Science Journal, Jan. 5, 2018: vol. 359, Issue 6371, pp. 61-651, Department of Mechanical Engineering & Materials Science and Engineering Program, University of Colorado, Boulder, CO 80309, USA.

* cited by examiner

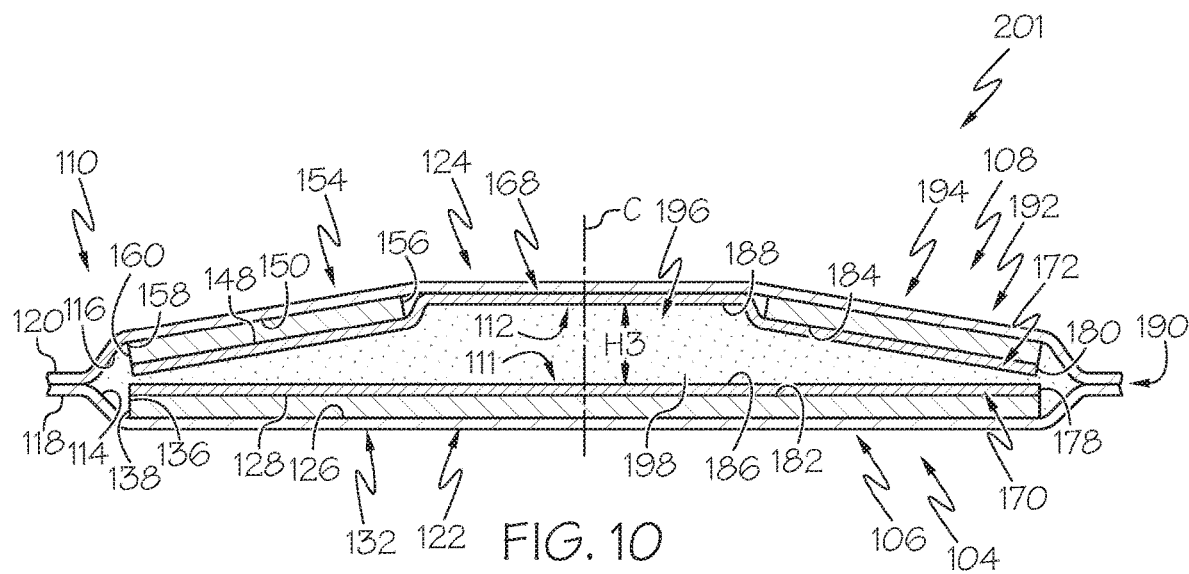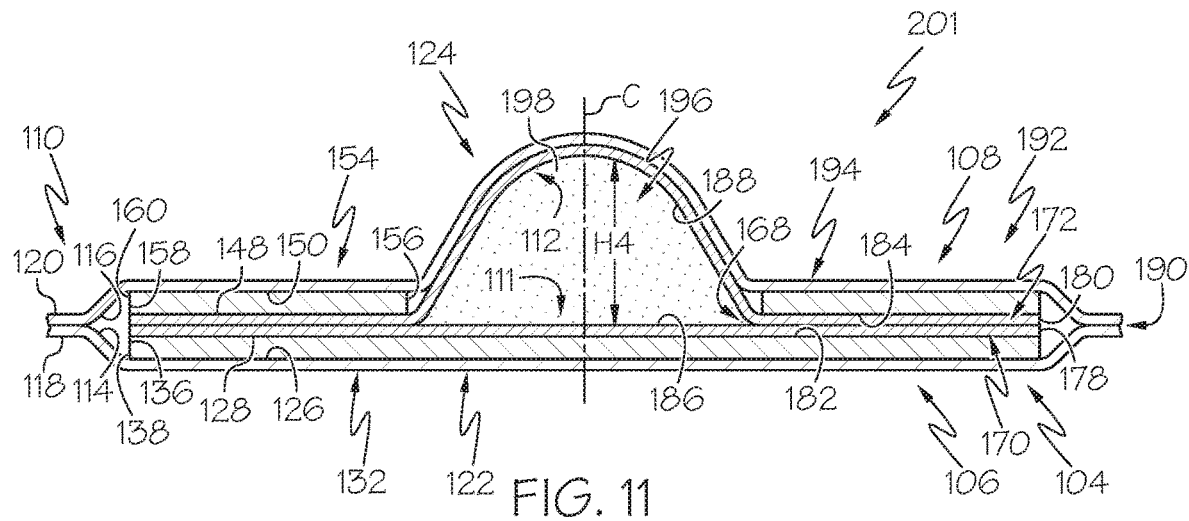

TEMPORARY CAST DEVICES COMPRISING ARTIFICIAL MUSCLES

TECHNICAL FIELD

The present specification generally relates to temporary cast devices and, in particular, to temporary cast devices that include artificial muscles for providing a select amount of pressure to an appendage of a user.

BACKGROUND

Temporary casts are often secured to or around an appendage of a user to treat orthopedic injuries, such as, but not limited to, bone fractures. A temporary cast may create internal environments between the temporary cast and the appendage of a user that may be uncomfortable for the user and elongate the healing process. For instance, localized swelling and inflammation are common biological responses to orthopedic injuries. Temporary casts may be unable to conform or adjust to the regions of the injured appendage experiencing inflammation, and thereby apply undesirably high pressures to the locally swollen regions of the appendage. By applying undesirably high pressures to an injured appendage of a user, temporary casts may cause pain and discomfort and restrict blood flow to and throughout the appendage, thereby hampering the healing process. Moreover, as a user is often unable to fully use or activate the appendage the temporary cast is applied to, the user may experience atrophy, stiffness, or other discomfort throughout the appendage. While some temporary casts may be adjustable by a user with hook and loop straps, for instance, that hold the temporary cast together, it is often difficult for an injured user to adjust the temporary cast, and the adjustment of the cast is imprecise (i.e. the user is unable to accurately select a desired pressure at a desired region of the temporary cast).

Accordingly, a need exists for temporary casts that may adjustably supply select pressures to an appendage of a user without greatly increasing the size or weight of the temporary cast with cumbersome hardware.

SUMMARY

In one embodiment, a temporary cast includes an exterior shell, a lining body including an inner layer, one or more pressure sensors communicatively coupled to a controller, and a plurality of artificial muscles disposed between the inner layer and the exterior shell. Each of the plurality of artificial muscles is communicatively coupled to the controller and includes a housing including an electrode region and an expandable fluid region, a dielectric fluid housed within the housing, and an electrode pair positioned in the electrode region of the housing. The electrode pair includes a first electrode fixed to a first surface of the housing and a second electrode fixed to a second surface of the housing, where the electrode pair is actuatable between a non-actuated state and an actuated state such that actuation from the non-actuated state to the actuated state directs the dielectric fluid into the expandable fluid region, expanding the expandable fluid region.

In another embodiment, a temporary cast includes an exterior shell and a lining body. The lining body is removably coupled to the exterior shell. The lining body further includes an inner layer and an outer layer, one or more pressure sensors communicatively coupled to a controller, and a plurality of stacks. Each stack of the plurality of stacks includes a plurality of artificial muscles communicatively coupled to the controller. Each of the plurality of artificial muscles includes a housing including an electrode region and an expandable fluid region, a dielectric fluid housed within the housing, and an electrode pair positioned in the electrode region of the housing. The electrode pair includes a first electrode fixed to a first surface of the housing and a second electrode fixed to a second surface of the housing, where the electrode pair is actuatable between a non-actuated state and an actuated state such that actuation from the non-actuated state to the actuated state directs the dielectric fluid into the expandable fluid region, expanding the expandable fluid region.

In yet another embodiment, a method for actuating a temporary cast, the method includes generating a voltage using a power supply electrically coupled to an electrode pair of an artificial muscle, the artificial muscle disposed in a cavity between an inner layer and an outer layer of a lining body. The artificial muscle comprises a housing having an electrode region and an expandable fluid region. The electrode pair is positioned in the electrode region of the housing. The electrode pair includes a first electrode fixed to a first surface of the housing and a second electrode fixed to a second surface of the housing. A dielectric fluid is housed within the housing. The method also includes applying the voltage to the electrode pair of the artificial muscle, thereby actuating the electrode pair from a non-actuated state to an actuated state such that the dielectric fluid is directed into the expandable fluid region of the housing and expands the expandable fluid region, thereby applying pressure to the inner layer of the lining body.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 10 schematically depicts a cross-sectional view of another illustrative artificial muscle in a non-actuated state, according to one or more embodiments shown and described herein;

FIG. 11 schematically depicts a cross-sectional view of the artificial muscle of FIG. 10 in an actuated state, according to one or more embodiments shown and described herein.

DETAILED DESCRIPTION

Figure 1:
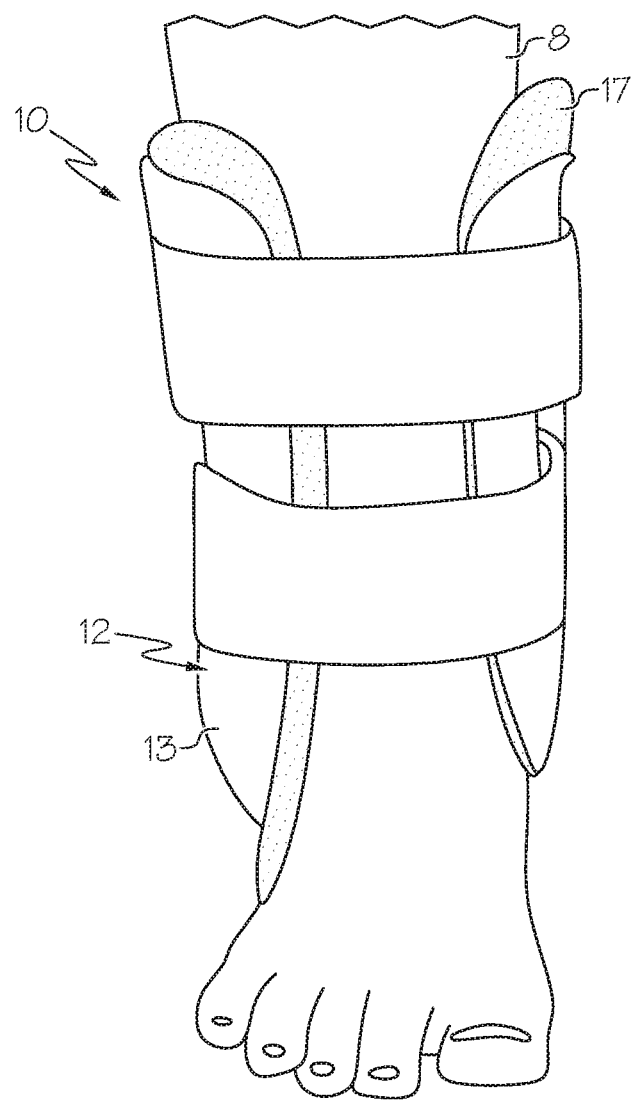
FIG. 1 schematically depicts a temporary cast on an appendage of a user, according to one or more embodiments shown and described herein.

Embodiments described herein are directed to temporary casts that include one or more artificial muscles configured to apply a selective pressure to an appendage of a user. The temporary casts described herein include a hard exterior shell and a lining body attached to an inner surface of the exterior shell. The lining body includes an outer layer attached to the exterior shell, an inner layer that contacts an appendage of a user when the temporary cast is worn on an appendage of a user, and a cavity between the inner and outer layers. The cavity includes the one or more artificial muscles, a portion of which contact the inner layer of the lining body, and one or more pressure sensors. The plurality of artificial muscles are actuatable to selectively raise and lower a region of the artificial muscles to provide a selective, on demand inflated expandable fluid region. In particular, the plurality of artificial muscles each include an electrode pair that may be drawn together by application of a voltage, thereby pushing dielectric fluid into the expandable fluid region, which applies localized pressure to the inner layer of the lining body. Actuation of the plurality of artificial muscles of the temporary cast may dynamically alter the pressure applied by the inner layer of the lining body to the appendage of the user, achieving select pressures at select locations along the lining body of the temporary cast. Various embodiments of the temporary cast and the operation of the temporary cast are described in more detail herein. Whenever possible, the same reference numerals will be used throughout the drawings to refer to the same or like parts.

Figure 3:
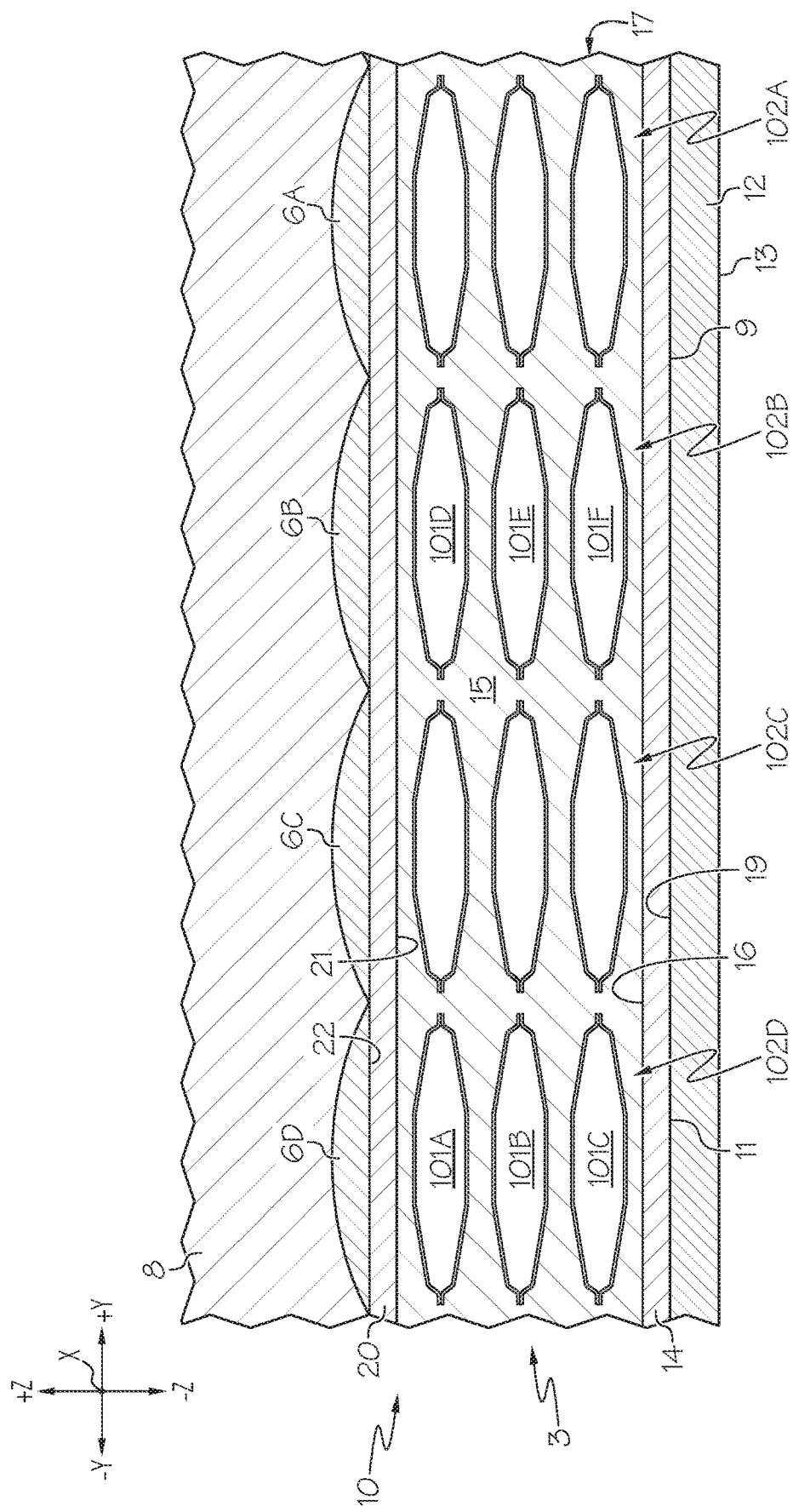
FIG. 3 schematically depicts a cross section of temporary cast and lining body of FIG. 2 on an appendage and in an non-actuated state, according to one or more embodiments shown and described herein.
Figure 4:
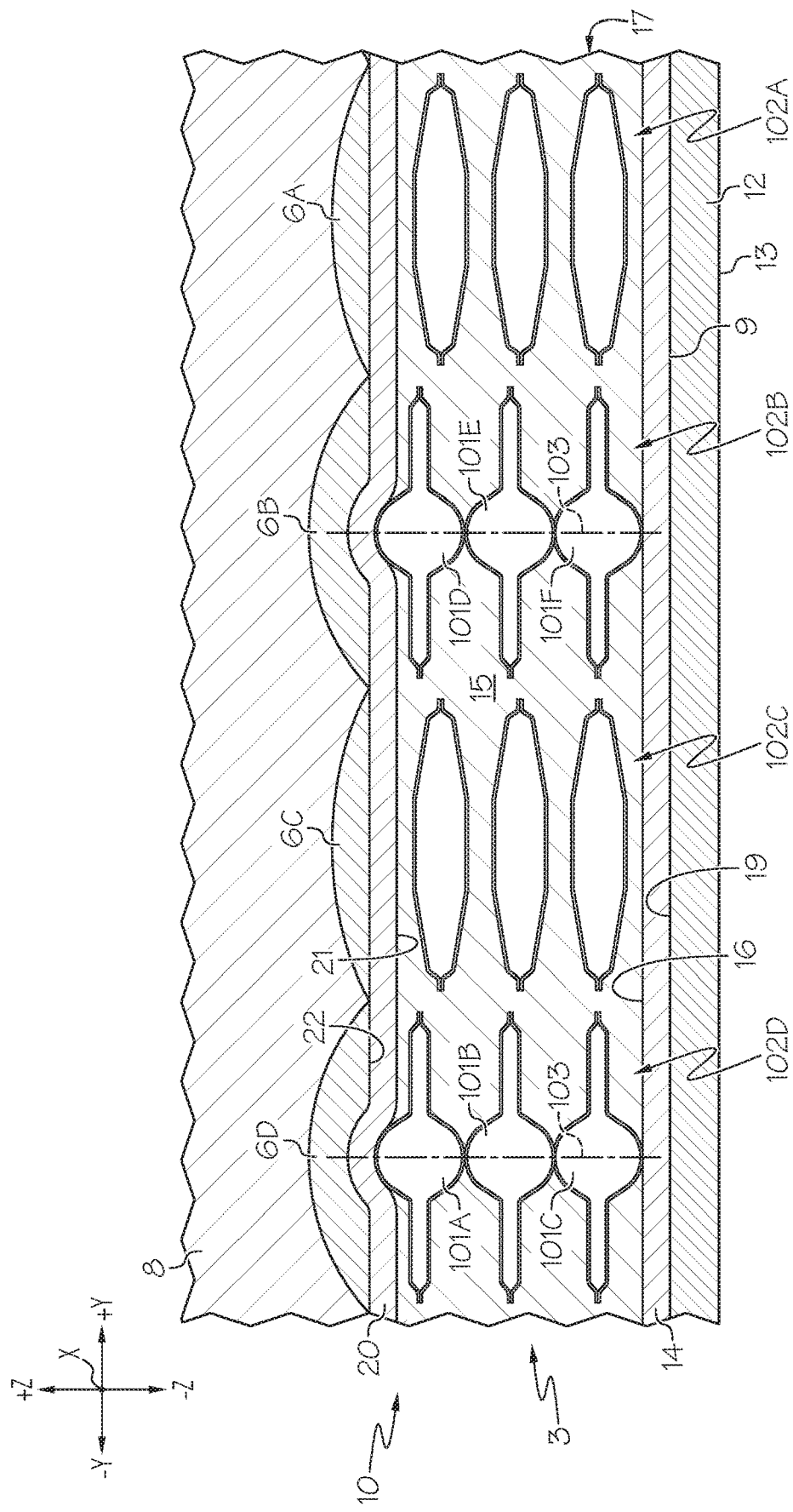
FIG. 4 schematically depicts a cross section of the temporary cast and lining body of FIG. 2 on an appendage and in an actuated state, according to one or more embodiments shown and described herein.

Referring now to FIG. 1, a temporary cast 10 is schematically depicted attached to an appendage 8 of a user. While the casts described herein are described as "temporary," it should be appreciated that this is a non-limiting description of the casts. In other words, while casts are traditionally worn by a user for a temporary amount of time (i.e. until an injury of the user heals), embodiments discussed herein could similarly be applied to semi-permanent or permanent casts, or casts designed to be worn by a user for any period of time. Furthermore, it should be appreciated that "appendage," as used herein, refers to any body part of a user. For instance, the temporary cast 10 may be worn on a limb, a neck, a torso, a hip, or any other desired body part of a user. The temporary cast 10 is depicted as a clamshell cast or brace. However, it should be appreciated that the temporary cast 10 may take the form of any known or yet-to-be developed cast design. The appendage 8 of the user is depicted as the lower leg or ankle of the user. The temporary cast 10 includes an exterior shell 12. The exterior shell 12 may be plastic or any other material of a desirable stiffness to stabilize and/or immobilize the appendage 8 and/or protect the appendage 8 from external forces likely to exacerbate an injury to the appendage 8. The exterior shell 12 includes an outer surface 13 and an inner surface 9 (FIGS. 3 and 4). The inner surface 9 of the exterior shell 12 is lined with a lining body 17. The lining body 17 includes a cavity 15, an outer layer 14 in contact with the inner surface of the exterior shell 12, and an inner layer 20 in contact with the appendage 8 (FIGS. 3 and 4). The lining body 17 may comprise a pliable material that is capable of conforming to the appendage 8 of the user. Accordingly, the lining body 17 may be described as "soft," and the exterior shell may be described as "hard." The lining body 17 may be removable and replaceable from the temporary cast 10, for example, using a removable attachment mechanism such as a hook and loop fastener (e.g., Velcro™), a removable adhesive, or the like. More specifically, the outer layer 14 may be fixedly or removably attached to the inner surface 9 of the exterior shell 12 at the outer surface 19 of the outer layer 14.

Figure 2:
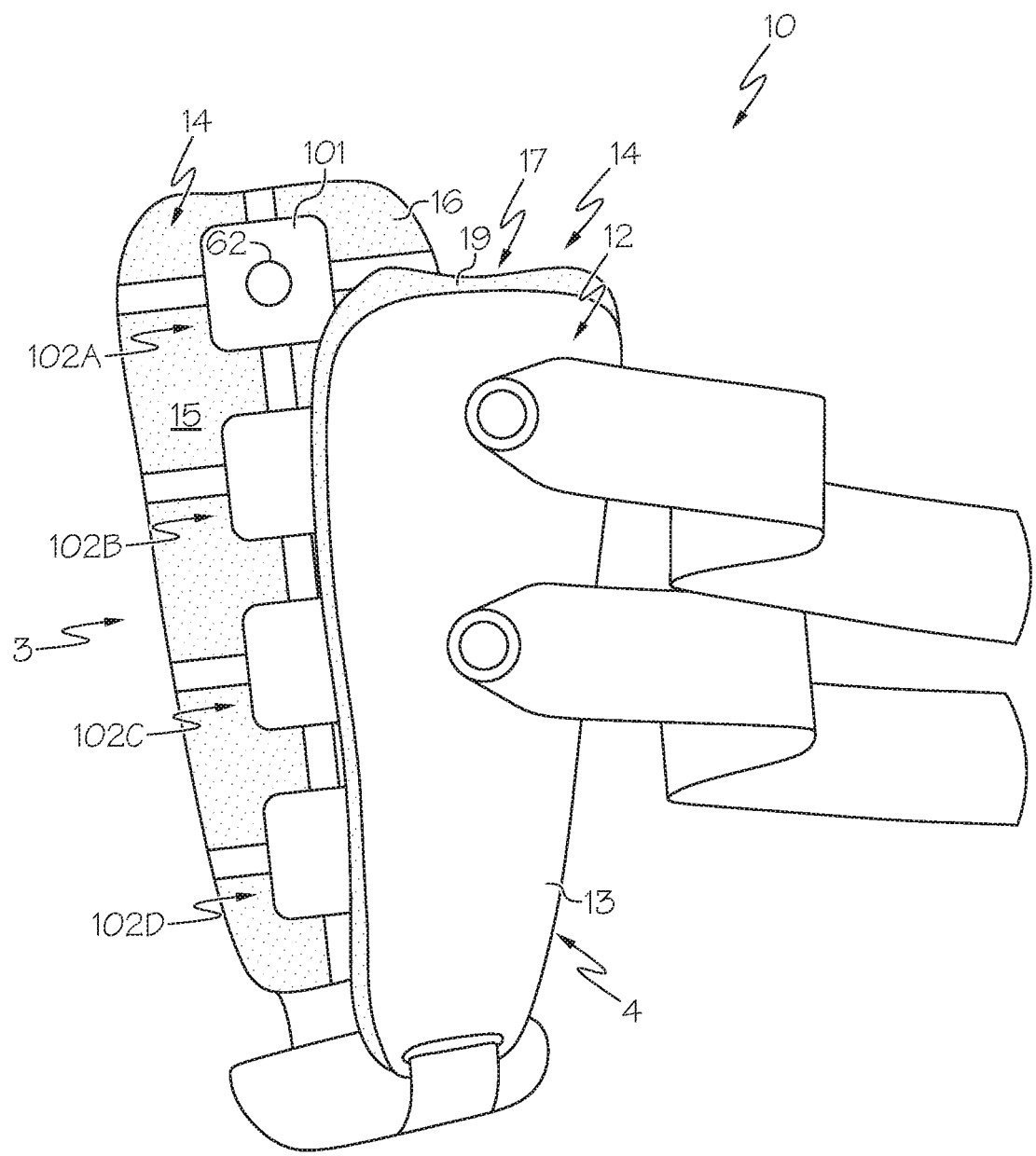
FIG. 2 schematically depicts a temporary cast and a lining body having a plurality of artificial muscles, according to one or more embodiments shown and described herein.

Referring now to FIG. 2, the temporary cast 10 is schematically depicted removed from an appendage of a user. As the temporary cast 10 is depicted as a clamshell cast or brace, it comprises two cast portions, a first cast portion 3 and a second cast portion 4, that may be secured together and around an appendage of a user with straps or other fasteners. It should be appreciated, however, that the temporary cast 10 may include more than two cast portions when the temporary cast 10 is a clamshell cast or brace. It should also be appreciated that in other embodiments, the temporary cast 10 may include a single, circumferentially continuous cast portion. The interior portion, or the portion facing the appendage 8 (depicted in FIG. 1) of the temporary cast 10 will now be discussed with reference to the first cast portion 3. However, it should be appreciated, that the same or similar description may also apply to the interior portion, or the portion facing the appendage 8, of the second cast portion 4.

Referring now to FIGS. 2-4, the first cast portion 3 of the temporary cast 10 is lined with the lining body 17 comprising the outer layer 14, the inner layer 20, and the cavity 15 disposed therebetween. The outer layer 14 includes an inner surface 16 and the cavity 15 is disposed between the inner surface 16 of the outer layer 14 and an outer surface 19 of the inner layer 20 of the lining body 17. A plurality of artificial muscles, including artificial muscle 101, are positioned within the cavity 15 of the lining body 17. While embodiments of the lining body 17 are described herein as comprising both the inner layer 20 and the outer layer 14, it should be understood that embodiments are contemplated comprising the inner layer 20 without the outer layer 14, where the inner layer 20 is directly coupled to the exterior shell 12 and the cavity 15 is disposed therebetween.

The cavity 15 of the lining body 17 may include a plurality of stacks of artificial muscles. More specifically, the lining body 17 may include stacks 102A, 102B, 102C, and 102D of artificial muscles 101. While the lining body 17 is depicted including four stacks 102A-D of artificial muscles 101, it should be appreciated that the lining body 17 may include any desirable number of stacks of artificial muscles 101. The lining body 17 may include stacks of artificial muscles 101 over the entire length and width of the lining body 17, and the lining body 17 may extend the entire length and width of the temporary cast 10. Accordingly, the number of stacks of artificial muscles 101 in the lining body 17 may depend on the length and width of the temporary cast 10 and the dimensions of the artificial muscles 101 employed in the lining body 17. For instance, the stacks of artificial muscles 101 may be considered to be in an array throughout the cavity 15 of the lining body 17. While the array of stacks 102A-D of artificial muscles are depicted in a 1×4 array in FIG. 2, depending on the length and width of the temporary cast 10, the array of stacks 102A-D of artificial muscles may be arranged in a 2×4 or 1×3 array, for instance. Each stack 102A-D of artificial muscles includes a plurality of artificial muscles 101 throughout the depth of the cavity 15. In other words, only the innermost artificial muscle of each stack 102A, 102B, 102C, and 102D of artificial muscles is depicted in FIG. 2. In embodiments, the lining body 17 of the temporary cast 10 may include a single layer of artificial muscles 101, in other words, the artificial muscles 101 of the lining body 17 may not be arranged in stacks of a plurality of artificial muscles 101 that traverse a depth of the cavity 15.

Referring to FIG. 2, the exterior shell 12 of the second cast portion 4 of the temporary cast 10 is depicted. It should be appreciated, however, that the following description similarly applies to the exterior shell of the first cast portion 3. Referring to FIGS. 2-4, the exterior shell 12 includes an outer surface 13 and an inner surface 9. The outer layer 14 of the lining body 17 of the second cast portion 4 includes an outer surface 19 that contacts the inner surface 9 of the exterior shell 12.

Referring to FIG. 2, a pressure sensor 62 may be disposed in the cavity 15, for example, coupled to the artificial muscle 101. The pressure sensor 62 is coupled to a housing 110 (FIG. 5) of the artificial muscle 101. In some embodiments, the artificial muscle 101 may include a plurality of pressure sensors 62. While the pressure sensor 62 is only depicted coupled to the artificial muscle 101, it should be appreciated that the innermost artificial muscle of each stack 102B, 102C, and 102D of artificial muscles may also include a pressure sensor. Indeed, in some embodiments, every artificial muscle within the cavity 15 of the lining body 17 may include a pressure sensor 62. In some embodiments, the pressure sensor 62 may be of any suitable type, such as, by way of non-limiting example, absolute, gauge, or differential pressure sensors. Sensing by the pressure sensor 62 may include any suitable technique such as resistive sensing, capacitive sensing, piezoelectric sensing, optical sensing, micro electro-mechanical system (MEMS), or any other suitable type of pressure sensing technique. Output from the pressure sensor 62 may be by millivolt-output transducers, volt-output transducers, transmitters, or any other suitable components.

In operation, the pressure sensor 62 may measure the pressure applied by the artificial muscle 101 and/or the stack 102A of artificial muscles to the inner layer of the lining body 17, and therefore to the appendage 8 (depicted in FIG. 1) of a user. Similarly, pressure sensors included in one or more artificial muscles throughout the stacks 102B-D of artificial muscles may measure pressure applied by the stacks 102B-D of artificial muscles to the inner layer of the lining body 17, and therefore to the appendage 8. In some embodiments, the pressure sensors 62 may be disposed in the cavity 15 without being coupled to individual artificial muscles 101. For example, in some embodiments, the pressure sensors 62 may be coupled to the outer surface 21 of the inner layer 20 and the inner surface 16 of the outer layer 14 of the lining body 17 (FIGS. 3 and 4). While the pressure sensor 62 is primarily described herein, it should be appreciated that the artificial muscle 101 may include any number of sensors to gather a variety of information on the internal environment of the temporary cast 10, or the environment between the temporary cast 10 and the appendage 8 (depicted in FIG. 1).

Figure 5:
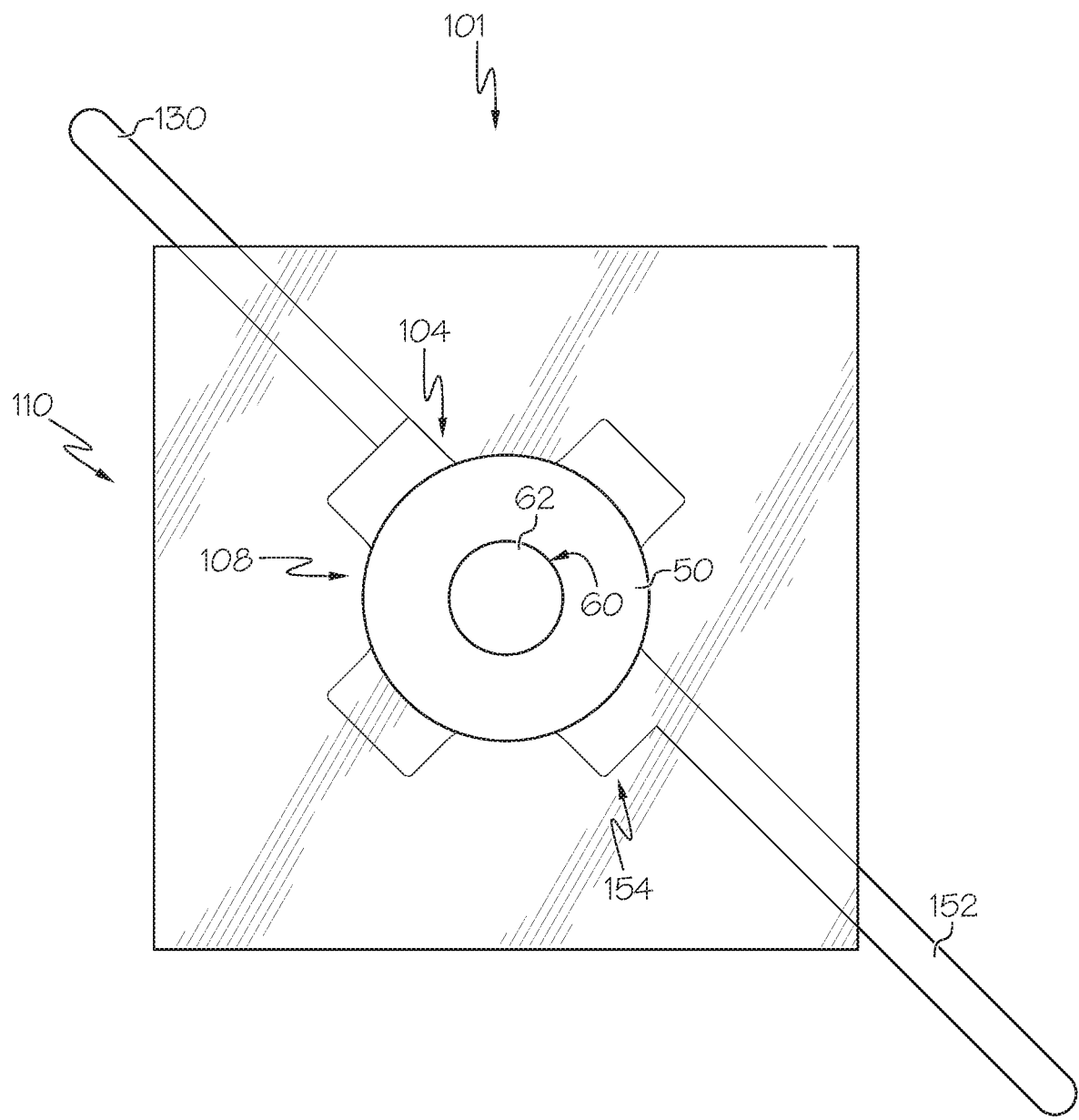
FIG. 5 schematically depict an illustrative artificial muscle of the temporary cast of FIGS. 1-4 with a sensor coupled to the illustrative artificial muscle, according to one or more embodiments shown and described herein.

With additional reference to FIG. 5, in some embodiments the pressure sensor 62 may be coupled to a housing 110 of an individual artificial muscle 101 in alignment with the expandable fluid region 196 (FIGS. 7-11) of the housing 110. Thus, the individual pressure sensor 62 can measure the pressure applied by the expandable fluid region 196 of the artificial muscle 101 to the inner layer 20 of the lining body 17 and thus applied to the appendage 8 (FIG. 1) when the artificial muscle 101 is actuated. Furthermore, the one or more pressure sensors 62 may measure the pressure applied by the inner layer 20 of the lining body 17 to the appendage 8 at one or more locations along the inner layer 20.

Referring again to FIGS. 2-4, in operation, each of the artificial muscles 101 may be independently actuatable to apply selective pressure to the inner layer 20 of the lining body 17 in response to one or more pressure measurements by the plurality of pressure sensors 62. For example, the pressure sensors 62 may measure a pressure applied to one or more locations of the inner layer 20 of the lining body 17 using the one or more pressure sensors 62 and actuate the plurality of artificial muscles 101 in a selective manner to apply selective pressure to the inner layer 20 of the lining body 17 in response to the pressure measurements by the one or more pressure sensors 62 at the one or more locations of the inner layer 20 of the lining body 17. In other words, the artificial muscles 101 may be selectively actuated to achieve a desired pressure based on the data gathered by the pressure sensors 62. In some embodiments, each stack 102A-D of artificial muscles may be independently actuatable to apply selective pressure to the inner layer 20 of the lining body 17 in response to one or more pressure measurements by the plurality of pressure sensors 62. For example, each artificial muscle 101D-F of the stack 102B of artificial muscles may be simultaneously actuated while the artificial muscles of the stacks 102A, 102C, and 102D of artificial muscles remain in a non-actuated state. Furthermore, actuation of each of the plurality of artificial muscles 101 may be controlled by an actuation system 400 (FIG. 12), which may include components housed in an onboard control unit 40 coupled to the lining body 17.

Referring now to FIGS. 3 and 4, a cross section of the temporary cast 10 in a non-actuated state (FIG. 3) and an actuated state (FIG. 4) is depicted. While FIGS. 3 and 4 depict cross sections of the first cast portion 3, it should be understood that the cross section of the second cast portion 4 (depicted in FIG. 2) may be substantially the same as the cross section of the first cast portion 3 depicted in FIGS. 3 and 4. The temporary cast 10 includes the exterior shell 12 having the outer surface 13 and an inner surface 9. The inner surface 22 of the inner layer 20 contacts the appendage 8 (FIG. 1) of the user. The inner layer 20, and particularly the inner surface 22, may be made of a soft, compliant, or elastic material that is able to conform to the appendage 8 of the user. The inner layer 20 may further be filled with a gel, liquid, or other material to enhance the compliance of the inner layer 20 and the ability of the inner layer 20 to comfortably conform to the appendage 8 of the user. The outer surface 21 of the inner layer 20 may additionally be made of a soft, compliant, or elastic material to enhance the ability of the inner layer 20 to conform to the appendage 8. The outer surface 21 of the inner layer 20 may contact at least one artificial muscle 101 of the lining body 17. The outer layer 14 may comprise the soft, compliant, or elastic material of the inner layer 20 or may comprise a more rigid material than the inner layer 20, such as a rigid plastic or polymeric material. One of the outer layer 14 and exterior shell 12 may remain rigid to provide a surface for the artificial muscles to push upwardly from. In some embodiments, the entire lining body 17 may comprise a non-absorbent material. Using a non-absorbent material facilitates ease of cleaning, particularly when the lining body 17 is removable from the exterior shell 12, allowing for repeated use by one or multiple different users.

As depicted in FIGS. 3 and 4 a plurality of artificial muscles 101 are disposed throughout the cavity 15 of the lining body 17. More specifically, the cavity 15 includes the stacks 102A, 102B, 102C, and 102D of artificial muscles. Each stack 102A-D of artificial muscles is shown to include a depth (e.g. in the z direction of the coordinate axes of FIGS. 3 and 4) of three artificial muscles. For instance, the stack 102D includes artificial muscles 101A, 101B, and 101C, and the stack 102B includes the artificial muscles 101D, 101E, and 101F. However, as explained above, the stacks 102A-D of artificial muscles may include any number of artificial muscles 101 throughout the depths of the stacks 102A-D. In some embodiments, six to twelve artificial muscles 101 may be included throughout the depth of the each stack 102A-D of artificial muscles. Similarly, while four stacks 102A-D of artificial muscles are depicted along the length (e.g. in the y direction of the coordinate axes of FIG. 3) of the lining body 17, it should be appreciated that any number of stacks may be disposed along the length of the lining body 17. It should also be appreciated that a plurality of stacks of artificial muscles 101 may further be located along the circumference or across the width (e.g. in the x direction of the coordinate axes of FIG. 3) of the lining body 17. Accordingly, an array of stacks of artificial muscles may span the entire outer surface 21 of the inner layer 20. In other embodiments, stacks of artificial muscles 101 may be located at select lengthwise (e.g. in the y direction of the coordinate axes of FIG. 3) and/or widthwise (e.g. in the x direction of the coordinate axes of FIG. 3) locations of the inner layer 20, either in a uniform or non-uniform array.

The plurality of artificial muscles 101 each include an electrode pair 104 disposed in a housing 110 together with a dielectric fluid 198 (FIGS. 6-11). The electrode pair 104 is disposed in an electrode region 194 of the housing 110, adjacent an expandable fluid region 196. In operation, voltage may be applied to the electrode pair 104, drawing the electrode pair 104 together, which directs dielectric fluid into the expandable fluid region 196, expanding the expandable fluid region 196. In operation, the lining body 17 is operable to apply selective pressure to the user by actuation of one or more of the plurality of artificial muscles 101. To actuate the lining body 17, voltage may be selectively applied to the one or more artificial muscles 101, expanding the expandable fluid regions 196 of the actuated artificial muscles 101. In some embodiments, each of the plurality of artificial muscles 101 are independently actuatable to apply selective pressure to the inner layer 20 of the lining body 17 which may apply pressure to the appendage 8 of the user when the temporary cast 10 is worn by a user. As will be discussed further below, depending on the magnitude of the voltage applied to each of the artificial muscles 101, the degree of actuation and pressure applied by the artificial muscles 101 may vary. In some embodiments, the expandable fluid region 196 of each artificial muscle 101 of each of the plurality of artificial muscle stacks 102A-D are coaxially aligned with one another. However, in other embodiments, there may be some offset between the expandable fluid region 196 of at least some of the artificial muscles of the plurality of artificial muscles stacks 102A-D.

Referring now to FIG. 4, each artificial muscle 101 of a stack of artificial muscles may be simultaneously and collectively actuated. In such embodiments, when a stack of artificial muscles is actuated, each artificial muscle 101 of the actuated stack may be actuated identically or to the same degree. In the illustrative example of FIG. 4, the stack 102D of artificial muscles is actuated and thus, the artificial muscles 101A, 101B, and 101C are actuated. The dielectric fluid 198 directed into the expandable fluid region 196 expands the expandable fluid region 196 of each artificial muscle 101A, 101B, and 101C (FIGS. 6-11). Therefore, the height (e.g. in the z direction of the coordinate axes of FIG. 4) of each artificial muscle 101A, 101B, and 101C, and therefore of the entire stack 102D of artificial muscles increases. As depicted in FIG. 4, the expandable fluid regions 196 of each artificial muscle 101A, 101B, and 101C of the stack 102D are coaxially aligned such that the axis of alignment 103 between the expandable fluid regions of the artificial muscles 101A, 101B, and 101C is substantially normal to the inner layer 20 and the appendage 8. When actuated, the stack 102D of artificial muscles, and more particularly the innermost artificial muscle of the stack 102D, artificial muscle 101A, applies a pressure to the inner layer 20, and specifically the outer surface 21 of the inner layer 20 of the lining body 17. Accordingly, the actuation of the stack 102D of artificial muscles applies a pressure to a portion 6D of the appendage 8 positioned above (e.g. in the +z direction of the coordinate axes of FIG. 4) or aligned with the stack 102D of artificial muscles.

In the illustrative example of FIG. 4, the stack 102B of artificial muscles is also actuated and thus the artificial muscles 101D, 101E, and 101F are actuated. When actuated, dielectric fluid 198 is directed into the expandable fluid region 196, expanding the expandable fluid region 196 of each artificial muscle 101D, 101E, and 101F (FIGS. 6-11). Therefore, the height (e.g. in the z direction of the coordinate axes of FIG. 4) of each of each artificial muscle 101D, 101E, and 101F, and therefore of the entire stack 102B of artificial muscles increases. The expandable fluid regions 196 of each artificial muscle 101D, 101E, and 101F of the stack 102B are coaxially aligned such that the axis of alignment 103 between the expandable fluid regions 196 of the artificial muscles 101D, 101E, and 101F is substantially normal to the inner layer 20 and the appendage 8. The stack 102B of artificial muscles, and more particularly the innermost artificial muscle of the stack 102B, artificial muscle 101D, applies a pressure to the inner layer 20, and specifically the outer surface 21 of the inner layer 20 of the lining body 17. Accordingly, the actuation of the stack 102B of artificial muscles applies a pressure to a portion 6B of the appendage 8 positioned above (e.g. in the +z direction of the coordinate axes of FIG. 4) or aligned with the stack 102B of artificial muscles.

In some embodiments in which each artificial muscle 101 of a stack of artificial muscles may be simultaneously and collectively actuated, each artificial muscle 101 of the actuated stack need not be identically actuated to the same degree. With reference to stack 102D of artificial muscles 101A-C, for instance, if the stack 102D is actuated, the artificial muscles 101A-C in the stack 102D are actuated. However, the artificial muscle 101A may be actuated to a first degree, the artificial muscle 101B may be actuated to a second degree, and the actuated muscle 101C may be actuated to a third degree. In FIG. 4, the stacks 102C and 102A of artificial muscles remain in a non-actuated state, illustrating that each stack 102 of artificial muscles may operate independent of one another.

While embodiment have been described wherein the artificial muscles 101 of each stack 102A-D of artificial muscles are aligned, or more specifically the expandable fluid regions 196 of the artificial muscles 101 are coaxially aligned such that the axes of alignment between the expandable fluid regions 196 of the artificial muscles 101 of each stack 102A-D are substantially normal to the inner layer 20 and the appendage 8, it should be appreciated that embodiments are also contemplated where the expandable fluid regions 196 of the artificial muscles 101 are not coaxially aligned. In other words, the artificial muscles 101 of each stack 102A-D may be in an offset, overlapping arrangement. This offset, overlapping arrangement is such that the expandable fluid regions 196 of the artificial muscles 101A-C in the stack 102D, for instance, are offset from each other. In other embodiments, a subset of the artificial muscles 101 of each stack 102A-D may remain coaxially aligned. For example, the expandable fluid regions 196 of the artificial muscles 101A and 101C may remain coaxially aligned, while the expandable fluid region of the artificial muscle 101B may be offset from the axis of alignment between the artificial muscles 101A and 101C.

Figure 12:
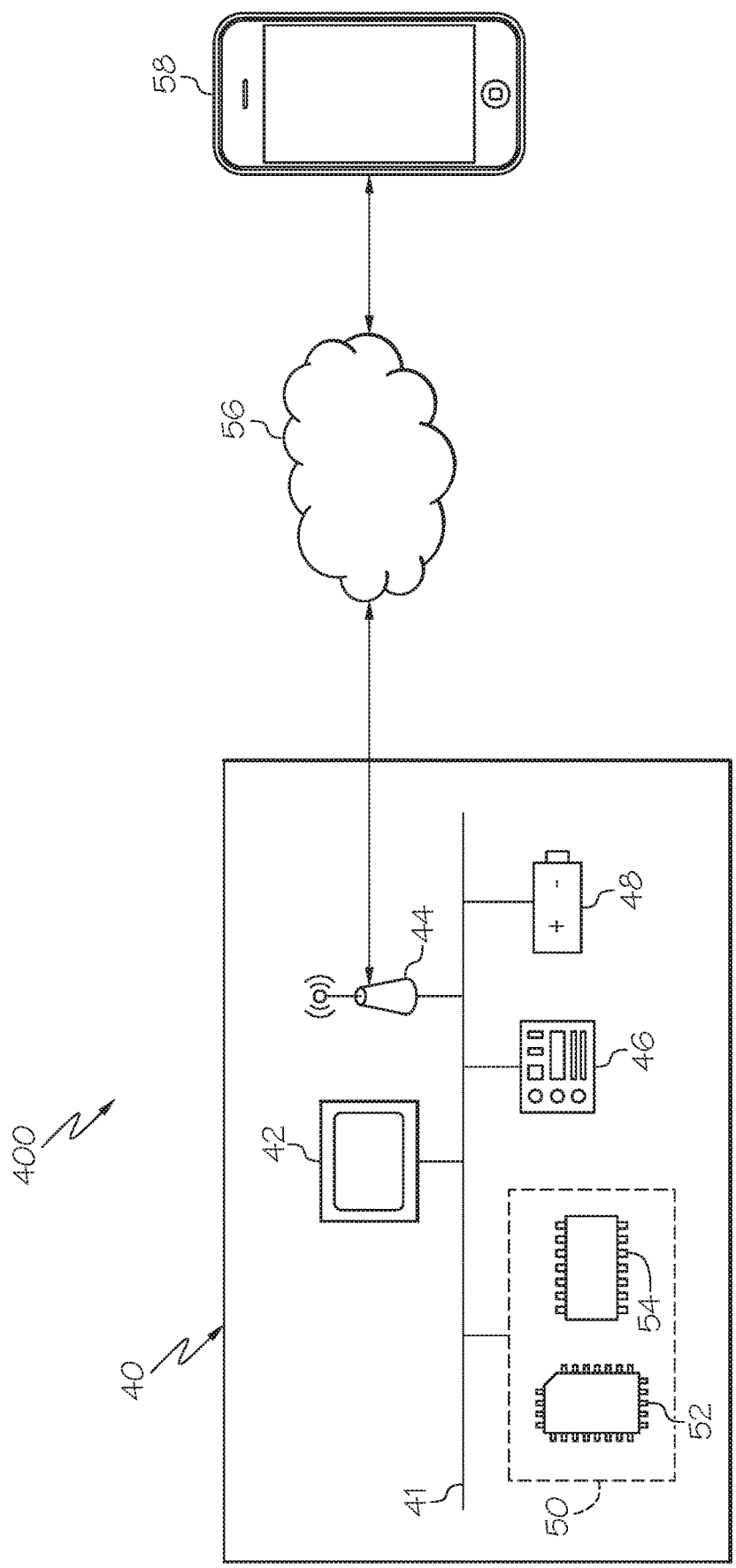
FIG. 12 schematically depicts an actuation system for operating the temporary cast of FIGS. 1-4, according to one or more embodiments shown and described herein.

In operation, a user may selectively actuate particular stacks of artificial muscles through the actuation system 400 (FIG. 12). A user may select a desired pressure for each stack 102A-D to independently apply to the appendage 8. For instance, the stack 102D may apply a first pressure to the portion 6D of the appendage 8, the stack 102C may apply a second pressure to a portion 6C of the appendage 8, the stack 102B may apply a third pressure to the portion 6B of the appendage 8, and the stack 102A may apply a fourth pressure to the portion 6A of the appendage 8. In some embodiments, the user may select a plurality of stacks of artificial muscles to actuate to the same degree and therefore apply the same pressure to the appendage 8. For instance, a user may wish a constant pressure to be applied along a select length (e.g. in the y direction of the coordinate axes FIG. 4) of the appendage 8 and therefore the lining body 17. In such embodiments, each of the stacks 102A-D, for instance, may be actuated to apply identical pressures to the appendage 8. Similarly, a user may wish a constant pressure to be applied along a select width (e.g. in the x direction of the coordinate axes of FIG. 4) of the appendage 8 and therefore the lining body 17. In such embodiments, the stack 102D, for instance, and additional stacks of artificial muscles aligned with the stack 102D in the x direction of the coordinate axes, or circumferentially, may be actuated to apply identical pressures to the appendage 8. A user may be supplied with a graphical display of the temporary cast 10 and/or specific coordinate locations of each of the stacks of artificial muscles in the temporary cast 10 to assist the user in selecting specific stacks of artificial muscles to actuate. In embodiments in which the temporary cast 10 consists of multiple portions, such as first cast portion 3 and second cast portion 4, actuation of a first stack in a first portion of the temporary cast 10 may result in the simultaneous actuation of a symmetrical stack in a second portion of the temporary cast 10. In other words, if a user selects to alter the actuation of a stack at a particular location in the array of stacks of a first portion of the temporary cast 10, the stack at an identical location within the array of stacks of a second portion of the temporary cast 10, will be actuated to the same degree.

A user may also actuate the stacks 102A-102D of artificial muscles in any desired pattern. For instance, a user may select for the temporary cast 10 to massage the appendage 8. In such cases, the actuation of the plurality of stacks 102A-D of artificial muscles may occur in rippling flows for a general massage effect. Indeed, the plurality of stacks 102A-D of artificial muscles may be actuated in a cascading, patterned, stochastic or uniform rhythm. Accordingly, a massage pattern or operation of actuation may include any mode of operation in which the pressure applied to the inner layer 20 and appendage 8 is temporally, spatially, or otherwise patterned (as opposed to maintaining or applying a constant pressure at the various points of the inner layer 20). Such massaging operations may remedy itches, stiffness, and/or soreness that the user experiences along the appendage 8.

The one or more pressure sensors 62 attached to a plurality of the artificial muscles 101 provide a user with a readout of the pressure presently applied by each stack 102A-D of artificial muscles to the portions 6A-6D of the appendage 8, respectively. Accordingly, the user may decisively select an updated pressure for each stack 102A-D to respectively apply to the appendage 8. Accordingly, the user's decision to increase or decrease pressure of the temporary cast 10 along the appendage 8 may be based on quantitative data instead of, or in addition to, the user's qualitative assessment of the pressures being applied to the appendage 8. For instance, through a user interface displaying data from the one or more pressure sensors 62, the user may identify a particular stack that is applying a pressure that is either greater or lesser than a desired pressure, and then selectively adjust the actuation of the stack to apply a known, quantitative pressure to the appendage 8. The pressure sensors 62 may also allow the temporary cast 10 to operate in a constant feedback loop. For instance, a user may want to maintain a constant pressure within the temporary cast 10, or more particularly, apply a constant pressure to the appendage 8. The appendage 8 may experience localized swelling. As such, the pressure between the temporary cast 10 and the appendage 8 in the areas of localized swelling may exceed a desired pressure. For instance, with respect to FIG. 4, the appendage 8 may swell at portions 6C and 6A. In response to such swelling, the pressure applied to the portions 6C and 6A of the appendage, as measured by the one or more pressure sensors, may exceed a desired pressure limit. Therefore, in response to such swelling, the stacks 102C and 102A may be relaxed or enter a non-actuated (as depicted in FIG. 4) or a lesser-actuated state to reduce the pressure on the portions 6C and 6A of the appendage 8 until a desirable pressure is achieved at the portions 6C and 6A. In contrast, the portions 6D and 6B of the appendage 8 may not experience swelling, and as such, the stacks 102D and 102B of artificial muscles may remain in a fully actuated state, for instance, to maintain a desired pressure at the portions 6D and 6B of the appendage 8. The controller 50 of the actuation system 400 (FIG. 12) may control such feedback loop operations. For instance, a user may first select a desired pressure to be maintained within the temporary cast 10. In other embodiments, the actuation system may be configured to determine the desired pressure based on the injury severity, injury location, patient data, and the like. The actuation system 400 may determine a first or initial pressure value applied to the inner layer 20 by the artificial muscles 101 from one or more pressure sensors 62. By comparing the initial pressure value with the desired pressure value, the actuation system 400 may then modify actuation of one or more artificial muscles 101 to change the pressure applied from the artificial muscles 101 to the inner layer 20 and achieve the desired pressure within the temporary cast 10.

While embodiments have been discussed wherein each artificial muscle 101 of a stack of artificial muscles is identically and simultaneously actuated, it should be appreciated that in some embodiments, individual artificial muscles 101 may be selectively actuated. More specifically, any artificial muscle 101 in the temporary cast 10 may be actuated, and actuated to a specific degree, independent of any other artificial muscle 101 in the temporary cast 10. For instance, with respect to the stack 102D of artificial muscles, each artificial muscle 101A, 101B, and 101C in the stack 102D may be independently actuated. Accordingly, the displacement of the stack 102D and the pressure applied by the stack 102D to the portion 6D of the appendage 8 may be altered by the number of artificial muscles of the stack 102D that are actuated. In other words, the artificial muscle 101C may be actuated to a specific degree, while the artificial muscles 101A and 101B may remain in a non-actuated state. Moreover, in embodiments in which the artificial muscles 101 in the cavity 15 of the lining body 17 are not arranged in stacks, but instead arranged as a single monolayer of artificial muscles 101 that contact the inner layer 20, each artificial muscle 101 in the monolayer may be independently actuated. In yet additional embodiments, the artificial muscles 101 may be neither arranged in stacks or a monolayer. In other words, the artificial muscles 101 may be randomly arranged throughout a depth the lining body 17 or arranged in multiple layers that do not substantially align or overlap to form linear stacks of artificial muscles throughout a depth of the lining body 17.

Figure 6:
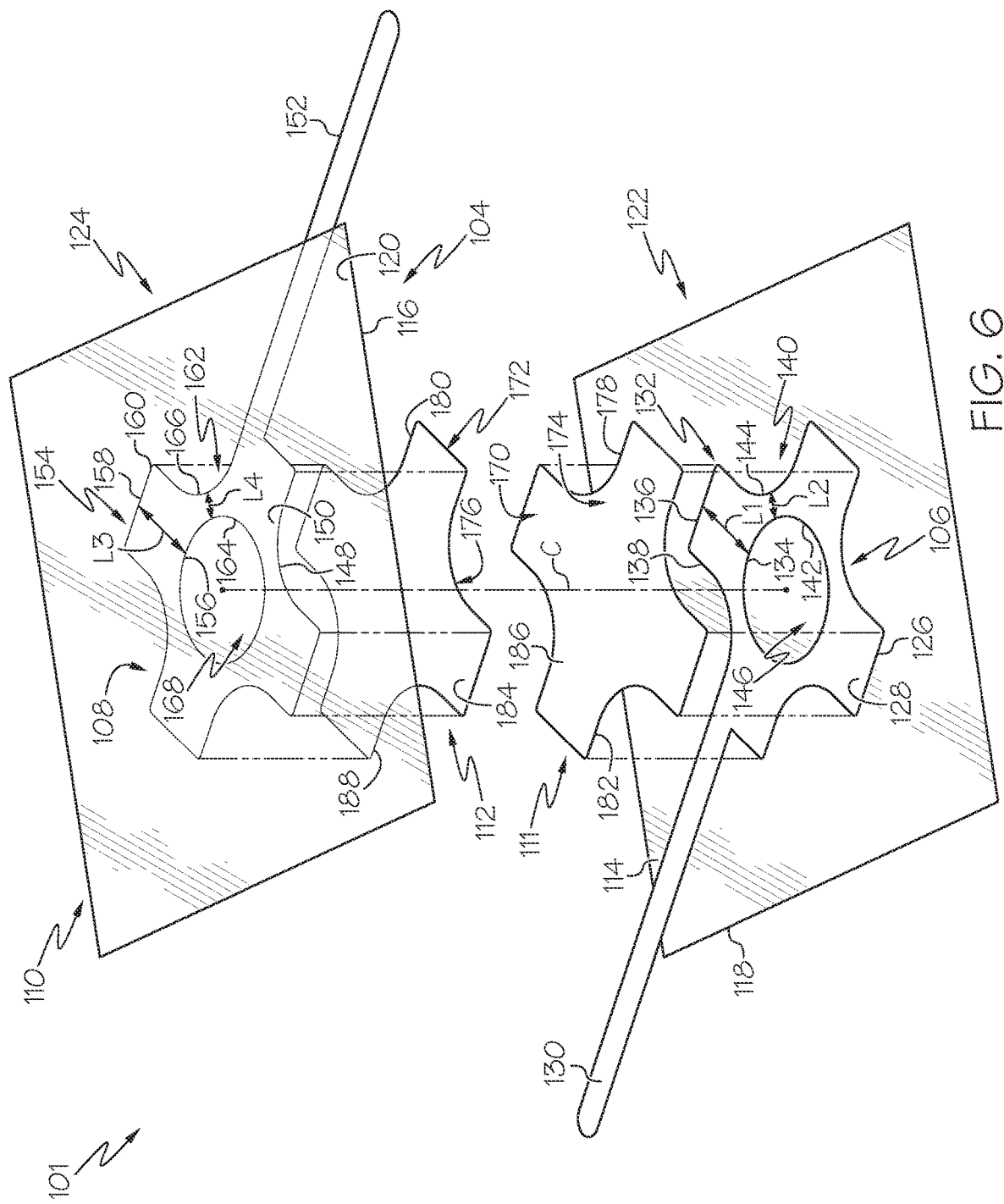
FIG. 6 schematically depicts an exploded view of an illustrative artificial muscle of the temporary cast of FIGS. 1-4, according to one or more embodiments shown and described herein.
Figure 7:
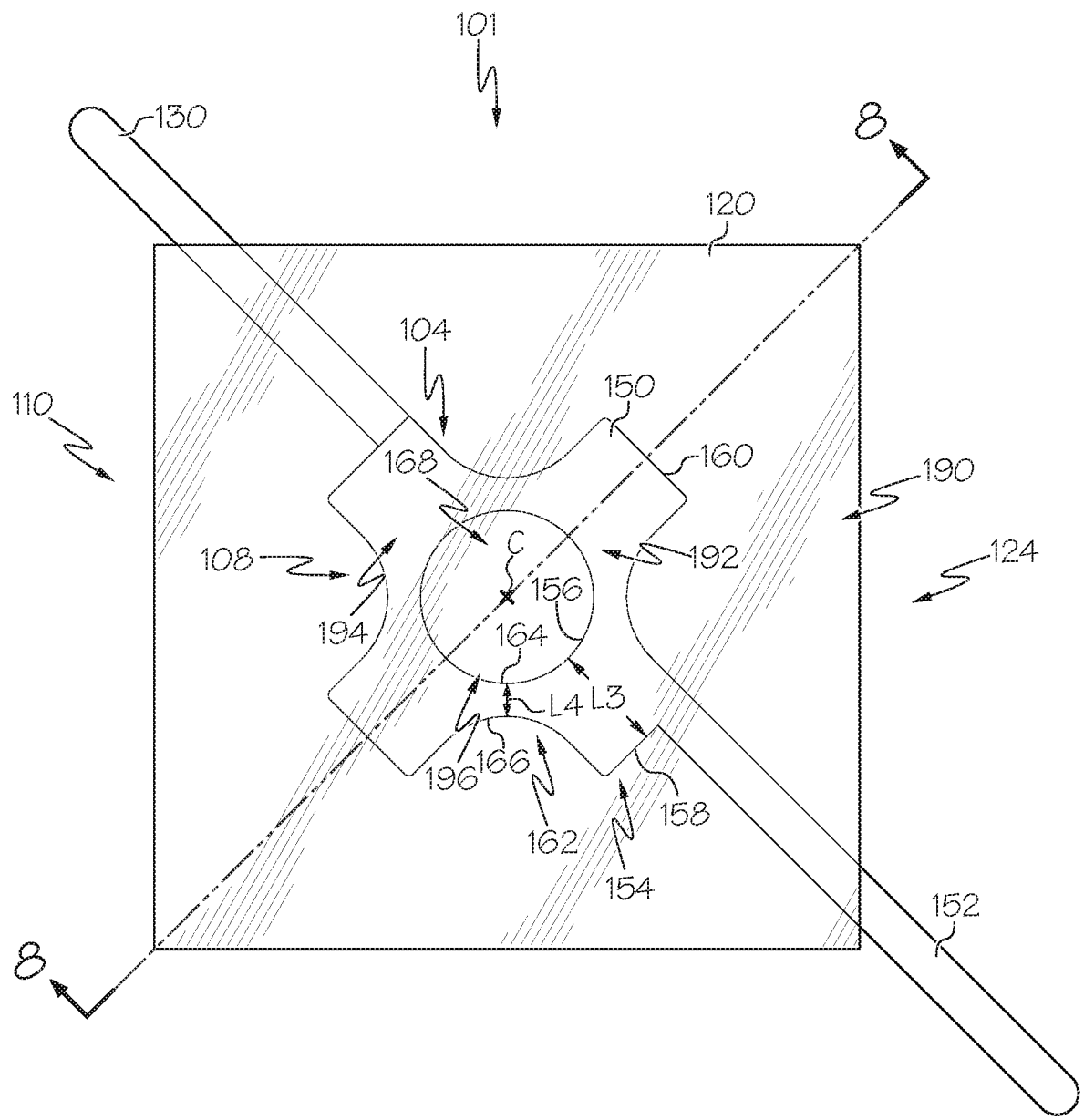
FIG. 7 schematically depicts a top view of the artificial muscle of FIG. 6, according to one or more embodiments shown and described herein.

Referring now to FIGS. 6 and 7, an example individual artificial muscle 101 of the plurality of artificial muscles of the temporary cast 10 is depicted in more detail. The artificial muscle 101 includes the housing 110, the electrode pair 104, including a first electrode 106 and a second electrode 108, fixed to opposite surfaces of the housing 110, a first electrical insulator layer 111 fixed to the first electrode 106, and a second electrical insulator layer 112 fixed to the second electrode 108. In some embodiments, the housing 110 is a one-piece monolithic layer including a pair of opposite inner surfaces, such as a first inner surface 114 and a second inner surface 116, and a pair of opposite outer surfaces, such as a first outer surface 118 and a second outer surface 120. In some embodiments, the first inner surface 114 and the second inner surface 116 of the housing 110 are heat-sealable. In other embodiments, the housing 110 may be a pair of individually fabricated film layers, such as a first film layer 122 and a second film layer 124. Thus, the first film layer 122 includes the first inner surface 114 and the first outer surface 118, and the second film layer 124 includes the second inner surface 116 and the second outer surface 120.

While the embodiments described herein primarily refer to the housing 110 as comprising the first film layer 122 and the second film layer 124, as opposed to the one-piece housing, it should be understood that either arrangement is contemplated. In some embodiments, the first film layer 122 and the second film layer 124 generally include the same structure and composition. For example, in some embodiments, the first film layer 122 and the second film layer 124 each comprises biaxially oriented polypropylene.

The first electrode 106 and the second electrode 108 are each positioned between the first film layer 122 and the second film layer 124. In some embodiments, the first electrode 106 and the second electrode 108 are each aluminum-coated polyester such as, for example, Mylar®. In addition, one of the first electrode 106 and the second electrode 108 is a negatively charged electrode and the other of the first electrode 106 and the second electrode 108 is a positively charged electrode. For purposes discussed herein, either electrode 106, 108 may be positively charged so long as the other electrode 106, 108 of the artificial muscle 101 is negatively charged.

The first electrode 106 has a film-facing surface 126 and an opposite inner surface 128. The first electrode 106 is positioned against the first film layer 122, specifically, the first inner surface 114 of the first film layer 122. In addition, the first electrode 106 includes a first terminal 130 extending from the first electrode 106 past an edge of the first film layer 122 such that the first terminal 130 can be connected to a power supply to actuate the first electrode 106. Specifically, the terminal is coupled, either directly or in series, to a power supply and a controller of an actuation system 400, as shown in FIG. 10. Similarly, the second electrode 108 has a film-facing surface 148 and an opposite inner surface 150. The second electrode 108 is positioned against the second film layer 124, specifically, the second inner surface 116 of the second film layer 124. The second electrode 108 includes a second terminal 152 extending from the second electrode 108 past an edge of the second film layer 124 such that the second terminal 152 can be connected to a power supply and a controller of the actuation system 400 to actuate the second electrode 108.

The first electrode 106 includes two or more tab portions 132 and two or more bridge portions 140. Each bridge portion 140 is positioned between adjacent tab portions 132, interconnecting these adjacent tab portions 132. Each tab portion 132 has a first end 134 extending radially from a center axis C of the first electrode 106 to an opposite second end 136 of the tab portion 132, where the second end 136 defines a portion of an outer perimeter 138 of the first electrode 106. Each bridge portion 140 has a first end 142 extending radially from the center axis C of the first electrode 106 to an opposite second end 144 of the bridge portion 140 defining another portion of the outer perimeter 138 of the first electrode 106. Each tab portion 132 has a tab length L1 and each bridge portion 140 has a bridge length L2 extending in a radial direction from the center axis C of the first electrode 106. The tab length L1 is a distance from the first end 134 to the second end 136 of the tab portion 132 and the bridge length L2 is a distance from the first end 142 to the second end 144 of the bridge portion 140. The tab length L1 of each tab portion 132 is longer than the bridge length L2 of each bridge portion 140. In some embodiments, the bridge length L2 is 20% to 50% of the tab length L1, such as 30% to 40% of the tab length L1.

In some embodiments, the two or more tab portions 132 are arranged in one or more pairs of tab portions 132. Each pair of tab portions 132 includes two tab portions 132 arranged diametrically opposed to one another. In some embodiments, the first electrode 106 may include only two tab portions 132 positioned on opposite sides or ends of the first electrode 106. In some embodiments, as shown in FIG. 6, the first electrode 106 includes four tab portions 132 and four bridge portions 140 interconnecting adjacent tab portions 132. In this embodiment, the four tab portion 132 are arranged as two pairs of tab portions 132 diametrically opposed to one another. Furthermore, as shown, the first terminal 130 extends from the second end 136 of one of the tab portions 132 and is integrally formed therewith.

Like the first electrode 106, the second electrode 108 includes at least a pair of tab portions 154 and two or more bridge portions 162. Each bridge portion 162 is positioned between adjacent tab portions 154, interconnecting these adjacent tab portions 154. Each tab portion 154 has a first end 156 extending radially from a center axis C of the second electrode 108 to an opposite second end 158 of the tab portion 154, where the second end 158 defines a portion of an outer perimeter 160 of the second electrode 108. Due to the first electrode 106 and the second electrode 108 being coaxial with one another, the center axis C of the first electrode 106 and the second electrode 108 are the same. Each bridge portion 162 has a first end 164 extending radially from the center axis C of the second electrode to an opposite second end 166 of the bridge portion 162 defining another portion of the outer perimeter 160 of the second electrode 108. Each tab portion 154 has a tab length L3 and each bridge portion 162 has a bridge length L4 extending in a radial direction from the center axis C of the second electrode 108. The tab length L3 is a distance from the first end 156 to the second end 158 of the tab portion 154 and the bridge length L4 is a distance from the first end 164 to the second end 166 of the bridge portion 162. The tab length L3 is longer than the bridge length L4 of each bridge portion 162. In some embodiments, the bridge length L4 is 20% to 50% of the tab length L3, such as 30% to 40% of the tab length L3.

In some embodiments, the two or more tab portions 154 are arranged in one or more pairs of tab portions 154. Each pair of tab portions 154 includes two tab portions 154 arranged diametrically opposed to one another. In some embodiments, the second electrode 108 may include only two tab portions 154 positioned on opposite sides or ends of the first electrode 106. In some embodiments, as shown in FIGS. 5-7, the second electrode 108 includes four tab portions 154 and four bridge portions 162 interconnecting adjacent tab portions 154. In this embodiment, the four tab portions 154 are arranged as two pairs of tab portions 154 diametrically opposed to one another. Furthermore, as shown, the second terminal 152 extends from the second end 158 of one of the tab portions 154 and is integrally formed therewith.

Figure 8:
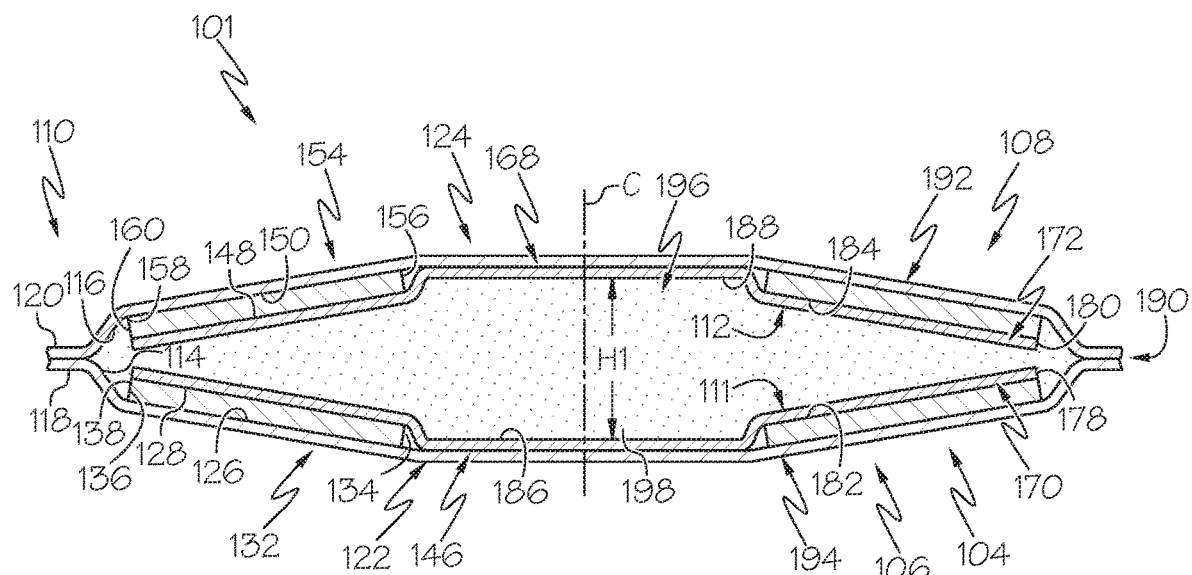
FIG. 8 schematically depicts a cross-sectional view of the artificial muscle of FIG. 7 taken along line 8-8 in FIG. 7 in a non-actuated state, according to one or more embodiments shown and described herein.
Figure 9:
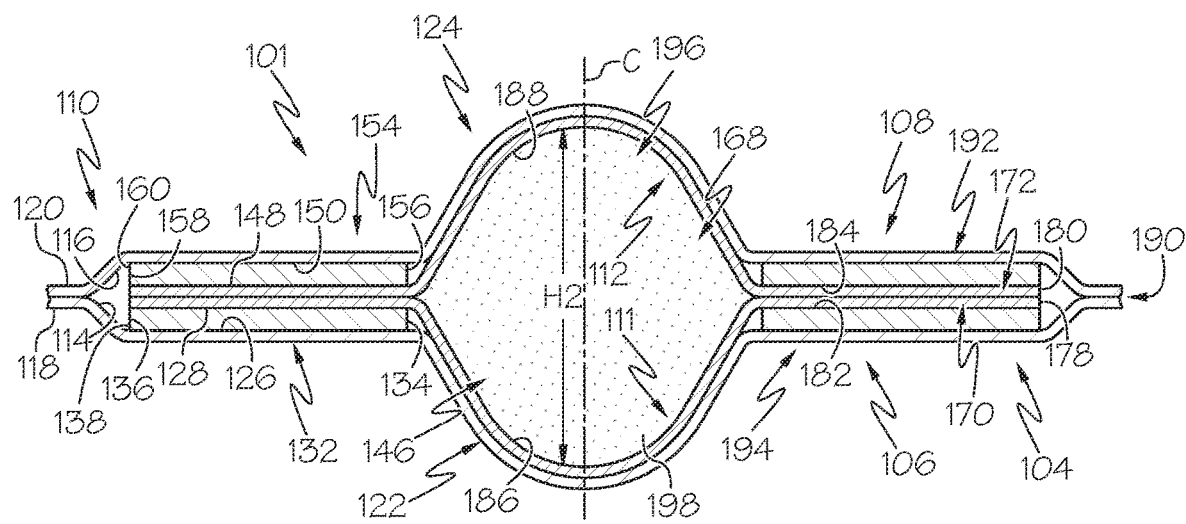
FIG. 9 schematically depicts a cross-sectional view of the artificial muscle of FIG. 7 taken along line 8-8 in FIG. 7 in an actuated state, according to one or more embodiments shown and described herein.

Referring now to FIGS. 6-11, at least one of the first electrode 106 and the second electrode 108 have a central opening formed therein between the first end 134 of the tab portions 132 and the first end 142 of the bridge portions 140. In FIGS. 8 and 9, the first electrode 106 has a central opening 146. However, it should be understood that the first electrode 106 does not need to include the central opening 146 when a central opening is provided within the second electrode 108, as shown in FIGS. 10 and 11. Alternatively, the second electrode 108 does not need to include the central opening when the central opening 146 is provided within the first electrode 106. Referring still to FIGS. 6-11, the first electrical insulator layer 111 and the second electrical insulator layer 112 have a geometry generally corresponding to the first electrode 106 and the second electrode 108, respectively. Thus, the first electrical insulator layer 111 and the second electrical insulator layer 112 each have tab portions 170, 172 and bridge portions 174, 176 corresponding to like portions on the first electrode 106 and the second electrode 108. Further, the first electrical insulator layer 111 and the second electrical insulator layer 112 each have an outer perimeter 178, 180 corresponding to the outer perimeter 138 of the first electrode 106 and the outer perimeter 160 of the second electrode 108, respectively, when positioned thereon.

It should be appreciated that, in some embodiments, the first electrical insulator layer 111 and the second electrical insulator layer 112 generally include the same structure and composition. As such, in some embodiments, the first electrical insulator layer 111 and the second electrical insulator layer 112 each include an adhesive surface 182, 184 and an opposite non-sealable surface 186, 188, respectively. Thus, in some embodiments, the first electrical insulator layer 111 and the second electrical insulator layer 112 are each a polymer tape adhered to the inner surface 128 of the first electrode 106 and the inner surface 150 of the second electrode 108, respectively.

Referring now to FIGS. 7-11, the artificial muscle 101 is shown in its assembled form with the first terminal 130 of the first electrode 106 and the second terminal 152 of the second electrode 108 extending past an outer perimeter of the housing 110, i.e., the first film layer 122 and the second film layer 124. As shown in FIG. 5, the second electrode 108 is stacked on top of the first electrode 106 and, therefore, the first electrode 106, the first film layer 122, and the second film layer 124 are not shown. In its assembled form, the first electrode 106, the second electrode 108, the first electrical insulator layer 111, and the second electrical insulator layer 112 are sandwiched between the first film layer 122 and the second film layer 124. The first film layer 122 is partially sealed to the second film layer 124 at an area surrounding the outer perimeter 138 of the first electrode 106 and the outer perimeter 160 of the second electrode 108. In some embodiments, the first film layer 122 is heat-sealed to the second film layer 124. Specifically, in some embodiments, the first film layer 122 is sealed to the second film layer 124 to define a sealed portion 190 surrounding the first electrode 106 and the second electrode 108. The first film layer 122 and the second film layer 124 may be sealed in any suitable manner, such as using an adhesive, heat sealing, or the like.

The first electrode 106, the second electrode 108, the first electrical insulator layer 111, and the second electrical insulator layer 112 provide a barrier that prevents the first film layer 122 from sealing to the second film layer 124 forming an unsealed portion 192. The unsealed portion 192 of the housing 110 includes the electrode region 194, in which the electrode pair 104 is provided, and the expandable fluid region 196, which is surrounded by the electrode region 194. The central openings 146, 168 of the first electrode 106 and the second electrode 108 form the expandable fluid region 196 and are arranged to be axially stacked on one another. Although not shown, the housing 110 may be cut to conform to the geometry of the electrode pair 104 and reduce the size of the artificial muscle 101, namely, the size of the sealed portion 190.

A dielectric fluid 198 is provided within the unsealed portion 192 and flows freely between the first electrode 106 and the second electrode 108. A "dielectric" fluid as used herein is a medium or material that transmits electrical force without conduction and as such has low electrical conductivity. Some non-limiting example dielectric fluids include perfluoroalkanes, transformer oils, and deionized water. It should be appreciated that the dielectric fluid 198 may be injected into the unsealed portion 192 of the artificial muscle 101 using a needle or other suitable injection device.

Referring now to FIGS. 8 and 9, the artificial muscle 101 is actuatable between a non-actuated state and an actuated state. In the non-actuated state, as shown in FIG. 8, the first electrode 106 and the second electrode 108 are partially spaced apart from one another proximate the central openings 146, 168 thereof and the first end 134, 156 of the tab portions 132, 154. The second end 136, 158 of the tab portions 132, 154 remain in position relative to one another due to the housing 110 being sealed at the outer perimeter 138 of the first electrode 106 and the outer perimeter 160 of the second electrode 108. In FIGS. 3 and 4, at least one of the one or more artificial muscles of the temporary cast 10 is in the non-actuated state. In the actuated state, as shown in FIG. 9, the first electrode 106 and the second electrode 108 are brought into contact with and oriented parallel to one another to force the dielectric fluid 198 into the expandable fluid region 196. This causes the dielectric fluid 198 to flow through the central openings 146, 168 of the first electrode 106 and the second electrode 108 and inflate the expandable fluid region 196. In FIG. 4, the artificial muscles 101A-F of the temporary cast 10 are in the actuated state.

Referring now to FIG. 8, the artificial muscle 101 is shown in the non-actuated state. The electrode pair 104 is provided within the electrode region 194 of the unsealed portion 192 of the housing 110. The central opening 146 of the first electrode 106 and the central opening 168 of the second electrode 108 are coaxially aligned within the expandable fluid region 196. In the non-actuated state, the first electrode 106 and the second electrode 108 are partially spaced apart from and non-parallel to one another. Due to the first film layer 122 being sealed to the second film layer 124 around the electrode pair 104, the second end 136, 158 of the tab portions 132, 154 are brought into contact with one another. Thus, dielectric fluid 198 is provided between the first electrode 106 and the second electrode 108, thereby separating the first end 134, 156 of the tab portions 132, 154 proximate the expandable fluid region 196. Stated another way, a distance between the first end 134 of the tab portion 132 of the first electrode 106 and the first end 156 of the tab portion 154 of the second electrode 108 is greater than a distance between the second end 136 of the tab portion 132 of the first electrode 106 and the second end 158 of the tab portion 154 of the second electrode 108. This results in the electrode pair 104 zippering toward the expandable fluid region 196 when actuated. In some embodiments, the first electrode 106 and the second electrode 108 may be flexible. Thus, as shown in FIG. 8, the first electrode 106 and the second electrode 108 are convex such that the second ends 136, 158 of the tab portions 132, 154 thereof may remain close to one another, but spaced apart from one another proximate the central openings 146, 168. In the non-actuated state, the expandable fluid region 196 has a first height H1.

When actuated, as shown in FIG. 9, the first electrode 106 and the second electrode 108 zipper toward one another from the second ends 144, 158 of the tab portions 132, 154 thereof, thereby pushing the dielectric fluid 198 into the expandable fluid region 196. As shown, when in the actuated state, the first electrode 106 and the second electrode 108 are parallel to one another. In the actuated state, the dielectric fluid 198 flows into the expandable fluid region 196 to inflate the expandable fluid region 196. As such, the first film layer 122 and the second film layer 124 expand in opposite directions. In the actuated state, the expandable fluid region 196 has a second height H2, which is greater than the first height H1 of the expandable fluid region 196 when in the non-actuated state. Although not shown, it should be noted that the electrode pair 104 may be partially actuated to a position between the non-actuated state and the actuated state. This would allow for partial inflation of the expandable fluid region 196 and adjustments when necessary.

In order to move the first electrode 106 and the second electrode 108 toward one another, a voltage is applied by a power supply (such as power supply 48 of FIG. 12). In some embodiments, a voltage of up to 10 kV may be provided from the power supply to induce an electric field through the dielectric fluid 198. The resulting attraction between the first electrode 106 and the second electrode 108 pushes the dielectric fluid 198 into the expandable fluid region 196. Pressure from the dielectric fluid 198 within the expandable fluid region 196 causes the first film layer 122 and the first electrical insulator layer 111 to deform in a first axial direction along the center axis C of the first electrode 106 and causes the second film layer 124 and the second electrical insulator layer 112 to deform in an opposite second axial direction along the center axis C of the second electrode 108. Once the voltage being supplied to the first electrode 106 and the second electrode 108 is discontinued, the first electrode 106 and the second electrode 108 return to their initial, non-parallel position in the non-actuated state.

It should be appreciated that the present embodiments of the artificial muscle 101 disclosed herein, specifically, the tab portions 132, 154 with the interconnecting bridge portions 174, 176, provide a number of improvements over actuators that do not include the tab portions 132, 154, such as hydraulically amplified self-healing electrostatic (HASEL) actuators described in the paper titled "Hydraulically amplified self-healing electrostatic actuators with muscle-like performance" by E. Acome, S. K. Mitchell, T. G. Morrissey, M. B. Emmett, C. Benjamin, M. King, M. Radakovitz, and C. Keplinger (Science 5 Jan. 2018: Vol. 359, Issue 6371, pp. 61-65). Embodiments of the artificial muscle 101 including two pairs of tab portions 132, 154 on each of the first electrode 106 and the second electrode 108, respectively, reduces the overall mass and thickness of the artificial muscle 101, reduces the amount of voltage required during actuation, and decreases the total volume of the artificial muscle 101 without reducing the amount of resulting force after actuation as compared to known HASEL actuators including donut-shaped electrodes having a uniform, radially-extending width. More particularly, the tab portions 132, 154 of the artificial muscle 101 provide zipping fronts that result in increased actuation power by providing localized and uniform hydraulic actuation of the artificial muscle 101 compared to HASEL actuators including donut-shaped electrodes. Specifically, one pair of tab portions 132, 154 provides twice the amount of actuator power per unit volume as compared to donut-shaped HASEL actuators, while two pairs of tab portions 132, 154 provide four times the amount of actuator power per unit volume. The bridge portions 174, 176 interconnecting the tab portions 132, 154 also limit buckling of the tab portions 132, 154 by maintaining the distance between adjacent tab portions 132, 154 during actuation. Because the bridge portions 174, 176 are integrally formed with the tab portions 132, 154, the bridge portions 174, 176 also prevent leakage between the tab portions 132, 154 by eliminating attachment locations that provide an increased risk of rupturing.

In operation, when the artificial muscle 101 is actuated, expansion of the expandable fluid region 196 produces a force of 3 Newton-millimeters (N.mm) per cubic centimeter (cm3) of actuator volume or greater, such as 4 N.mm per cm3 or greater, 5 N.mm per cm3 or greater, 6 N.mm per cm3 or greater, 7 N.mm per cm3 or greater, 8 N.mm per cm3 or greater, or the like. In one example, when the artificial muscle 101 is actuated by a voltage of 9.5 kilovolts (kV), the artificial muscle 101 provides a resulting force of 5 N. In another example, when the artificial muscle 101 is actuated by a voltage of 10 kV the artificial muscle 101 provides 440% strain under a 500 gram load.

Moreover, the size of the first electrode 106 and the second electrode 108 is proportional to the amount of displacement of the dielectric fluid 198. Therefore, when greater displacement within the expandable fluid region 196 is desired, the size of the electrode pair 104 is increased relative to the size of the expandable fluid region 196. It should be appreciated that the size of the expandable fluid region 196 is defined by the central openings 146, 168 in the first electrode 106 and the second electrode 108. Thus, the degree of displacement within the expandable fluid region 196 may alternatively, or in addition, be controlled by increasing or reducing the size of the central openings 146, 168.

As shown in FIGS. 10 and 11, another embodiment of an artificial muscle 201 is illustrated. The artificial muscle 201 is substantially similar to the artificial muscle 101. As such, like structure is indicated with like reference numerals. However, as shown, the first electrode 106 does not include a central opening. Thus, only the second electrode 108 includes the central opening 168 formed therein. As shown in FIG. 10, the artificial muscle 201 is in the non-actuated state with the first electrode 106 being planar and the second electrode 108 being convex relative to the first electrode 106. In the non-actuated state, the expandable fluid region 196 has a first height H3. In the actuated state, as shown in FIG. 11, the expandable fluid region 196 has a second height H4, which is greater than the first height H3. It should be appreciated that by providing the central opening 168 only in the second electrode 108 as opposed to both the first electrode 106 and the second electrode 108, the total deformation may be formed on one side of the artificial muscle 201. In addition, because the total deformation is formed on only one side of the artificial muscle 201, the second height H4 of the expandable fluid region 196 of the artificial muscle 201 extends further from a longitudinal axis perpendicular to the central axis C of the artificial muscle 201 than the second height H2 of the expandable fluid region 196 of the artificial muscle 101 when all other dimensions, orientations, and volume of dielectric fluid are the same. It should be understood that embodiments of the artificial muscle 201 may be used together with or in place of the one or more artificial muscles 101 of the temporary cast 10 of FIGS. 2-4.

Referring now to FIG. 12, an actuation system 400 may be provided for operating the temporary cast 10, in particular, for operating the plurality of artificial muscles 101 of the temporary cast 10, for example, based on sensor measurements of the one or more pressure sensors 62, instructions provided by a user, or a combination thereof. The actuation system 400 may comprise a controller 50, an operating device 46, a power supply 48, a display device 42, network interface hardware 44, and a communication path 41 communicatively coupled these components, some or all of which may be disposed in the onboard control unit 40. Furthermore, the actuation system 400 may be communicatively coupled to the plurality of artificial muscles 101 and the one or more pressure sensors 62.

The controller 50 comprises a processor 52 and a non-transitory electronic memory 54 to which various components are communicatively coupled. In some embodiments, the processor 52 and the non-transitory electronic memory 54 and/or the other components are included within a single device. In other embodiments, the processor 52 and the non-transitory electronic memory 54 and/or the other components may be distributed among multiple devices that are communicatively coupled. The controller 50 includes non-transitory electronic memory 54 that stores a set of machine-readable instructions. The processor 52 executes the machine-readable instructions stored in the non-transitory electronic memory 54. The non-transitory electronic memory 54 may comprise RAM, ROM, flash memories, hard drives, or any device capable of storing machine-readable instructions such that the machine-readable instructions can be accessed by the processor 52. Accordingly, the actuation system 400 described herein may be implemented in any conventional computer programming language, as pre-programmed hardware elements, or as a combination of hardware and software components. The non-transitory electronic memory 54 may be implemented as one memory module or a plurality of memory modules.

In some embodiments, the non-transitory electronic memory 54 includes instructions for executing the functions of the actuation system 400. The instructions may include instructions for operating the temporary cast 10, for example, and instructions for actuating the plurality of artificial muscles 101, individually and/or simultaneously and collectively in stacks.

The processor 52 may be any device capable of executing machine-readable instructions. For example, the processor 52 may be an integrated circuit, a microchip, a computer, or any other computing device. The non-transitory electronic memory 54 and the processor 52 are coupled to the communication path 41 that provides signal interconnectivity between various components and/or modules of the actuation system 400. Accordingly, the communication path 41 may communicatively couple any number of processors with one another, and allow the modules coupled to the communication path 41 to operate in a distributed computing environment. Specifically, each of the modules may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

As schematically depicted in FIG. 12, the communication path 41 communicatively couples the processor 52 and the non-transitory electronic memory 54 of the controller 50 with a plurality of other components of the actuation system 400. For example, the actuation system 400 depicted in FIG. 12 includes the processor 52 and the non-transitory electronic memory 54 communicatively coupled with the operating device 46 and the power supply 48.

The operating device 46 allows for a user to control operation of the plurality of artificial muscles 101 of the temporary cast 10. In some embodiments, the operating device 46 may be a switch, toggle, button, or any combination of controls to provide user operation. The operating device 46 is coupled to the communication path 41 such that the communication path 41 communicatively couples the operating device 46 to other modules of the actuation system 400. The operating device 46 may provide a user interface for receiving user instructions as to a specific operating configuration of the temporary cast 10, such as an operating configuration to alter the pressure between the inner layer 20 and the appendage 8 by actuating user-selected stacks or individual artificial muscles 101, to operate the temporary cast 10 in a feedback loop such that the pressure between the inner layer 20 and the appendage is automatically adjusted based on the pressure sensor 62 readings to maintain a desired pressure, or to operate the temporary cast 10 in a massage or rhythmic pattern of actuation. Additional operating configurations of the temporary cast 10 may also be selected by the user through the user interface.

The power supply 48 (e.g., battery) provides power to the one or more artificial muscles of the temporary cast 10. In some embodiments, the power supply 48 is a rechargeable direct current power source. It is to be understood that the power supply 48 may be a single power supply or battery for providing power to the one or more artificial muscles of the temporary cast 10. A power adapter (not shown) may be provided and electrically coupled via a wiring harness or the like for providing power to the plurality of artificial muscles of the temporary cast 10 via the power supply 48.

In some embodiments, the actuation system 400 also includes a display device 42. The display device 42 is coupled to the communication path 41 such that the communication path 41 communicatively couples the display device 42 to other modules of the actuation system 400. The display device 42 may be located on the temporary cast 10, for example, as part of the onboard control unit 40, and may output a notification in response to an actuation state of the artificial muscles 101 of the temporary cast 10 or indication of a change in the actuation state of the one or more artificial muscles 101 of the temporary cast 10. The display device 42 may also display sensor measurements, such as pressure measurements performed by the one or more pressure sensors 62. Moreover, the display device 42 may be a touchscreen that, in addition to providing optical information, detects the presence and location of a tactile input upon a surface of or adjacent to the display device 42. Accordingly, the display device 42 may include the operating device 46 and receive mechanical input directly upon the optical output provided by the display device 42.

In some embodiments, the actuation system 400 includes network interface hardware 44 for communicatively coupling the actuation system 400 to a portable device 58 via a network 56. The portable device 58 may include, without limitation, a smartphone, a tablet, a personal media player, or any other electric device that includes wireless communication functionality. It is to be appreciated that, when provided, the portable device 58 may serve to provide user commands to the controller 50, instead of the operating device 46. As such, a user may be able to control or set a program for controlling the artificial muscles 101 of the temporary cast 10 utilizing the controls of the operating device 46. Thus, the artificial muscles 101 of the temporary cast 10 may be controlled remotely via the portable device 58 wirelessly communicating with the controller 50 via the network 56.

It should now be understood that embodiments described herein are directed to temporary casts that include a plurality of artificial muscles disposed in a cavity of a lining body between an inner layer and an outer layer of the lining body. The artificial muscles are actuatable to selectively apply pressure to the inner layer to apply a selective and customizable pressure to an appendage of a user that the temporary cast is worn on. The lining body further includes one or more pressure sensors operable to measure the localized pressures applied to the inner layer and appendage of the user by the artificial muscles. The selective and customizable actuation of the plurality of artificial muscles may adjust the pressure distribution applied to an appendage of a user, increasing using comfort and expediting a healing process of the appendage.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A temporary cast comprising:
an exterior shell;
a lining body comprising an inner layer;
one or more pressure sensors communicatively coupled to a controller; and
a plurality of artificial muscles disposed between the inner layer and the exterior shell, wherein:
each of the plurality of artificial muscles is communicatively coupled to the controller; and
each of the plurality of artificial muscles comprises:
a housing comprising an electrode region and an expandable fluid region;
a dielectric fluid housed within the housing; and
an electrode pair positioned in the electrode region of the housing, the electrode pair comprising a first electrode fixed to a first surface of the housing and a second electrode fixed to a second surface of the housing, the first electrode and the second electrode each comprising two or more tab portions and two or more bridge portions, each of the two or more bridge portions interconnecting adjacent tab portions of the two or more tab portions, at least one of the first electrode and the second electrode comprising a central opening positioned between the two or more tab portions and encircling the expandable fluid region, wherein the electrode pair is actuatable between a non-actuated state and an actuated state such that actuation from the non-actuated state to the actuated state directs the dielectric fluid into the expandable fluid region, expanding the expandable fluid region.

2. The temporary cast of claim 1, wherein:
the lining body further comprises an outer layer, wherein:
the outer layer is attached to the exterior shell;
the inner layer and the outer layer define a cavity therebetween; and
the plurality of artificial muscles are disposed within the cavity.

3. The temporary cast of claim 1, wherein:
the inner layer and the exterior shell define a cavity therebetween; and
the plurality of artificial muscles are disposed within the cavity.

4. The temporary cast of claim 1, wherein the first electrode and the second electrode each includes two pairs of tab portions and two pairs of bridge portions, each tab portion diametrically opposing an opposite tab portion.

5. The temporary cast of claim 1, wherein:
when the electrode pair is in the non-actuated state, the first electrode and the second electrode are non-parallel to one another; and
when the electrode pair is in the actuated state, the first electrode and the second electrode are parallel to one another, such that the first electrode and the second electrode are configured to zipper toward one another and toward the central opening when actuated from the non-actuated state to the actuated state.

6. The temporary cast of claim 1, wherein the plurality of artificial muscles are arranged in a stack such that the expandable fluid region of each artificial muscle in the stack is coaxially aligned.

7. The temporary cast of claim 6, wherein an axis of alignment of the plurality of artificial muscles in the stack is normal to the inner layer of the lining body.

8. The temporary cast of claim 6, wherein the each of the plurality of artificial muscles in the stack are collectively actuatable such that each of the plurality of artificial muscles in the stack are simultaneously actuated or non-actuated.

9. The temporary cast of claim 1, wherein the controller is configured to:
determine an initial pressure value from the one or more pressure sensors, wherein the initial pressure value indicates a pressure applied from the plurality of artificial muscles to the inner layer; and
modify actuation of the plurality of artificial muscles to achieve a desired pressure value, wherein the desired pressure value indicates a pressure applied from the plurality of artificial muscles to the inner layer that is different than the initial pressure value.

10. The temporary cast of claim 9, wherein a consistent amount of pressure applied to the inner layer is maintained based upon a feedback loop maintained by the controller in coordination with the one or more pressure sensors.

11. The temporary cast of claim 1, wherein the controller is configured to accept instructions input from a user and modify actuation of the plurality of artificial muscles based on the instructions.

12. The temporary cast of claim 1, wherein the one or more pressure sensors are each respectively coupled to the housing of an individual artificial muscle of the plurality of artificial muscles.

13. The temporary cast of claim 12, wherein each of the one or more pressure sensors are respectively coupled to the housing of the individual artificial muscle of the plurality of artificial muscles in alignment with the expandable fluid region of the housing.

14. A temporary cast comprising:
an exterior shell; and
a lining body, wherein:
the lining body is removably coupled to the exterior shell; and
the lining body further comprises:
an inner layer and an outer layer;
one or more pressure sensors communicatively coupled to a controller; and
a plurality of stacks, each stack of the plurality of stacks comprising a plurality of artificial muscles communicatively coupled to the controller, wherein:
each of the plurality of artificial muscles comprises:
a housing comprising an electrode region and an expandable fluid region;
a dielectric fluid housed within the housing;
an electrode pair positioned in the electrode region of the housing, the electrode pair comprising a first electrode fixed to a first surface of the housing and a second electrode fixed to a second surface of the housing, the first electrode and the second electrode each comprising two or more tab portions and two or more bridge portions, each of the two or more bridge portions interconnecting adjacent tab portions of the two or more tab portions, at least one of the first electrode and the second electrode comprising a central opening positioned between the two or more tab portions and encircling the expandable fluid region wherein the electrode pair is actuatable between a non-actuated state and an actuated state such that actuation from the non-actuated state to the actuated state directs the dielectric fluid into the expandable fluid region, expanding the expandable fluid region.

15. The temporary cast of claim 14, wherein each of the plurality of stacks are independently actuatable.

16. A method for actuating a temporary cast, the method comprising:
generating a voltage using a power supply electrically coupled to an electrode pair of an artificial muscle, the artificial muscle disposed in a cavity between an inner layer and an outer layer of a lining body, wherein:
the artificial muscle comprises a housing having an electrode region and an expandable fluid region;
the electrode pair is positioned in the electrode region of the housing;
the electrode pair comprises a first electrode fixed to a first surface of the housing and a second electrode fixed to a second surface of the housing, the first electrode and the second electrode each comprising two or more tab portions and two or more bridge portions, each of the two or more bridge portions interconnecting adjacent tab portions of the two or more tab portions, and at least one of the first electrode and the second electrode comprising a central opening positioned between the two or more tab portions and encircling the expandable fluid region; and
a dielectric fluid is housed within the housing; and
applying the voltage to the electrode pair of the artificial muscle, thereby actuating the electrode pair from a non-actuated state to an actuated state such that the dielectric fluid is directed into the expandable fluid region of the housing and expands the expandable fluid region, thereby applying pressure to the inner layer of the lining body.

17. The method of claim 16, wherein the artificial muscle is one of a plurality of artificial muscles disposed in the cavity of the lining body.

18. The method of claim 17, further comprising:
measuring a pressure applied to the inner layer of the lining body using one or more pressure sensors disposed in the cavity of the lining body; and
applying the voltage to the plurality of artificial muscles in a selective manner to apply selective pressure to the inner layer of the lining body in response to pressure measurements at the inner layer of the lining body.

* * * * *